(12) United States Patent
Pamplona et al.

(10) Patent No.: US 9,844,323 B2
(45) Date of Patent: Dec. 19, 2017

(54) METHODS AND APPARATUS FOR EYE RELAXATION

(71) Applicant: EyeNetra, Inc., Somerville, MA (US)

(72) Inventors: Vitor Pamplona, Somerville, MA (US); Ramesh Raskar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/906,272

(22) PCT Filed: Jul. 20, 2013

(86) PCT No.: PCT/US2013/051412
§ 371 (c)(1),
(2) Date: Jan. 20, 2016

(87) PCT Pub. No.: WO2015/012784
PCT Pub. Date: Jan. 29, 2015

(65) Prior Publication Data
US 2016/0157716 A1      Jun. 9, 2016

(51) Int. Cl.
*A61B 3/02*    (2006.01)
*A61B 3/18*    (2006.01)
*A61B 3/103*   (2006.01)

(52) U.S. Cl.
CPC .............. *A61B 3/18* (2013.01); *A61B 3/103* (2013.01)

(58) Field of Classification Search
CPC ........... A61B 3/14; A61B 3/024; A61B 3/032; A61B 3/02; A61B 3/08; A61B 3/10; A61B 3/113
(Continued)

(56) References Cited

U.S. PATENT DOCUMENTS 3,843,240 A   10/1974   Cornsweet
5,555,039 A    9/1996   Iki et al.
(Continued)

FOREIGN PATENT DOCUMENTS

EP   0135736 A2   4/1985
WO   9300854 A1   1/1993
(Continued)

OTHER PUBLICATIONS

Amplona, V., Tailored displays to compensate for visual aberrations. ACM Transactions on Graphics (TOG)—Proceedings of ACM SIGGRAPH 2012, vol. 31 Issue 4, Article No. 81, Jul. 2012, ACM New York, NY, USA.

*Primary Examiner* — Hung Dang
(74) *Attorney, Agent, or Firm* — Stephen R. Otis

(57) ABSTRACT

In exemplary implementations of this invention, a bi-ocular apparatus presents visual stimuli to one eye of a human subject in order to relax that eye, while measuring refractive aberration of the subject's other eye. Alternately, a monocular device presents stimuli to relax an eye while testing the same eye. The apparatus induces eye relaxation by displaying virtual objects at varying apparent distances from the subject. For example, the apparatus may do so by (i) changing distance between a backlit film and a lens; (ii) using extra lenses; (iii) using an adaptive lens that changes power; (v) selecting distinct positions in a progressive or multi-focal length lens; (vi) selecting distinct optical depths by fiber optical illumination; (vii) displaying a 3D virtual image at any given apparent depth; or (viii) display both a warped version of the real world and a test image at the same time.

15 Claims, 20 Drawing Sheets

(58) Field of Classification Search
USPC ....... 351/206, 205, 246, 209, 221, 212, 239, 351/240
See application file for complete search history.

(56) References Cited

U.S. PATENT DOCUMENTS

| | | |
|---|---|---|
| 5,612,754 A | 3/1997 | Tanaka |
| 7,338,166 B2 * | 3/2008 | Waldorf ................ A61B 3/112 351/205 |
| 2006/0087618 A1 | 4/2006 | Smart et al. |
| 2013/0027668 A1 | 1/2013 | Pamplona et al. |

FOREIGN PATENT DOCUMENTS

| | | |
|---|---|---|
| WO | 9511473 A1 | 4/1995 |
| WO | 2008091611 A1 | 7/2008 |

\* cited by examiner

Y

Z

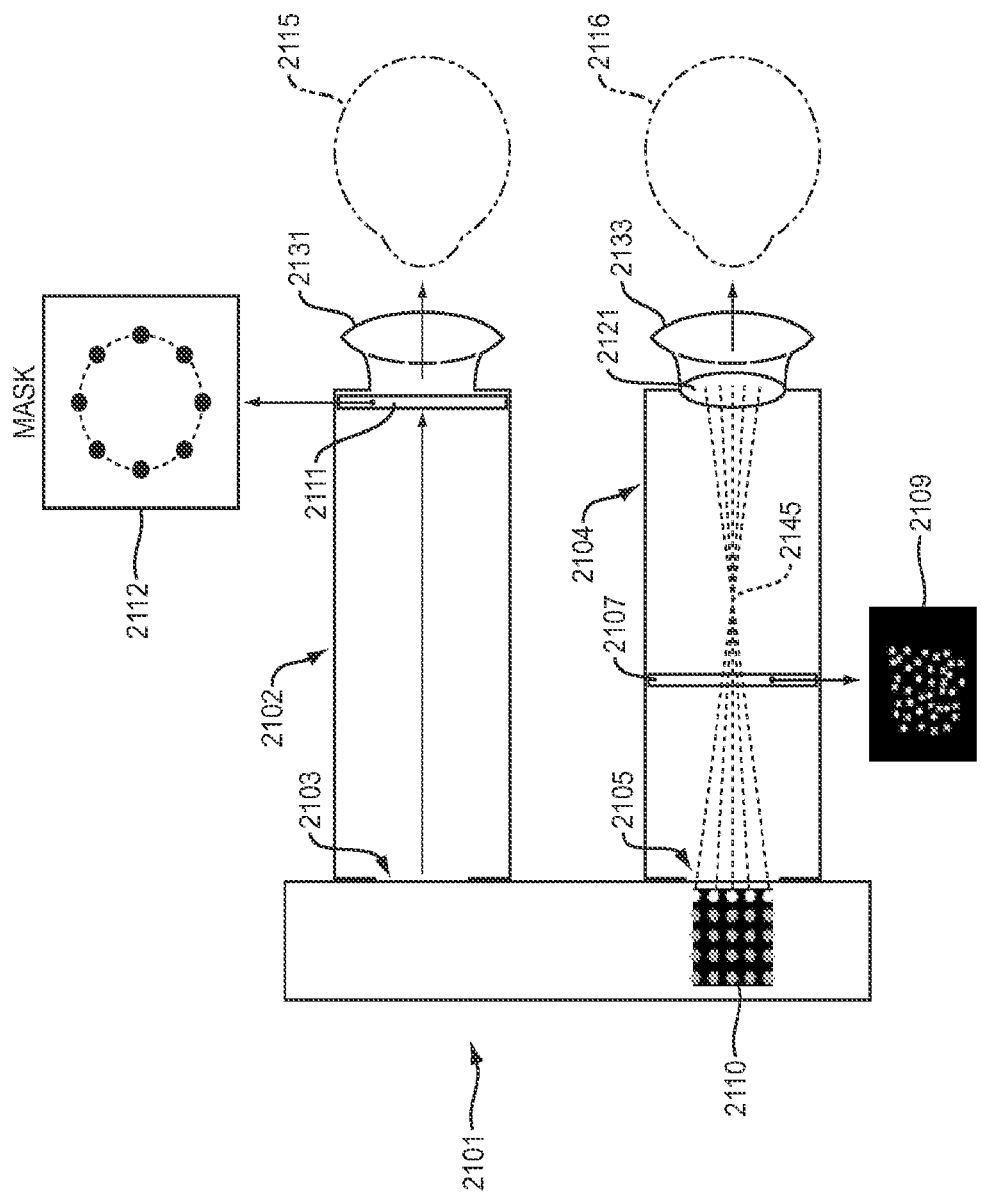

METHODS AND APPARATUS FOR EYE RELAXATION

FIELD OF THE TECHNOLOGY

The present invention relates generally to tests for refractive aberration.

BACKGROUND

When eye muscles that control the shape of the crystalline lens of a human eye are fully relaxed, a healthy eye tends to focus far away, theoretically "at infinity". Accommodation is the process by which eye muscles tense in order to change the shape of the crystalline lens, and thereby to change the distance at which the eye is focused.

It is desirable, when testing for refractive aberration of an eye, to control the accommodation (or inversely, the relaxation) of the eye. In many cases, during the testing, it is desirable for the eye muscles to be fully relaxed, reaching the furthest point the testing eye can focus.

Nearsighted individuals (myopia) cannot focus at infinity. Their furthest point of focus is before infinity. For example, a 1D (1 diopter) myope can focus at maximum of 1 meter. Farsighted individuals (hyperopia) can focus optically "beyond infinity". Placing the eye focus at that point is desired to measure the correct degree of hyperopia.

Convergence is the simultaneous inward movement of eyes toward each other (e.g., when children cross their eyes in jest). Convergence impacts accommodation. Parallel eyes (looking straight ahead with no convergence) drive relaxation of the lens. Converged eyes drive accommodation (focus) to the converged point, affecting the readings of any refractive measurement device.

SUMMARY

In exemplary implementations of this invention, a bi-ocular apparatus presents visual stimuli to one eye of a human subject in order to relax that eye, while measuring refractive aberration of the subject's other eye. Alternately, a monocular device presents stimuli to relax an eye while testing the same eye.

The apparatus induces eye relaxation by displaying virtual objects at varying apparent distances from the subject. For example, the apparatus may do so by (i) changing distance between a backlit film and a lens; (ii) by a procedure of adding extra lenses; (iii) using an adaptive lens that changes its power/focal length; (v) stimulating through distinct positions in a progressive or multi-focal length lens; (vi) selecting distinct optical depths by fiber optical illumination; (vii) displaying a 3D virtual image at any apparent depth by, for example, using an additional electronic mask (e.g., an LCD); or (viii) displaying both a warped version of the real world and a test image at the same time.

As used herein, an eye whose refractive aberrations are being tested is a "test eye". An eye whose refractive aberrations are not being tested is an "idle eye".

Depending on the particular implementation of this invention, a bi-ocular device may present relaxation stimuli to only the idle eye, or may present it to both the test and idle eyes. Or, for example, a monocular device may present relaxation stimuli to the test eye.

In both bi-ocular and monocular implementations, the apparatus induces an eye to relax by creating an illusion of depth, displaying virtual objects at given depths. For example, as an idle eye focuses on an apparently far distant object, the muscles of the idle eye tend to relax. The muscles of the test eye tend to follow suit.

The apparatus may be affixed to or include a handheld display device (e.g., a cell phone or smartphone). A display screen of the display device may display (i) an optical test, (ii) relaxation patterns, or (iii) an illumination pattern for backlighting for optical elements in the apparatus (or any combination of these).

It is desirable, when testing for refractive aberration of an eye, to control convergence. The visual stimuli presented to an idle eye may be duplicated to the testing eye to create a stereo view and help to relax lens through the convergence or divergence of the eyes. When the eyes converge to a closer point, the eyes tend to accommodate to focus at that spatial depth. When the eyes converge to infinity (looking straight), the eyes tend to focus at infinity, relaxing their ciliary muscles, and creating a favorable condition for measuring myopia. Convergence is correlated with accommodation/relaxation, but if the image is optically beyond infinity, the eye relaxes to focus beyond infinity even if convergence is to infinity only.

In some implementations of this invention, eye relaxation is induced in accordance with principles of this invention, while refractive aberration is measured using methods and apparatus described in the NETRA patent application As used herein, the "NETRA patent application" means international patent application PCT/US2011/03368, which application was filed on the 22 of Apr. 2011 and published as WO 2011/133945 A1 on 27 Oct. 2011. As used herein, "NETRA" means the Near Eye Tool for Refractive Assessment, and methods of making and using same, which are described in the NETRA patent application.

However, this invention is not limited to use with NETRA. It can be used in any other context, including for any test for refractive aberration. For example, this invention can be used for subjective/manifest refraction, auto-refractors and retinoscopy.

The description of the present invention in the Summary and Abstract sections hereof is just a summary. It is intended only to give a general introduction to some illustrative implementations of this invention. It does not describe all of the details of this invention. This invention may be implemented in many other ways.

BRIEF DESCRIPTION OF THE DRAWINGS

FIG. 21 shows a bi-ocular apparatus with masks that are creating an image of a virtual 3D object.

The above Figures show some illustrative implementations of this invention, or provide information that relates to those implementations. However, this invention may be implemented in many other ways. The above Figures do not show all of the details of this invention.

DETAILED DESCRIPTION

Lens and Film:

In some implementations of this invention, a lens and film are used to present stimuli to an idle eye.

Figure 1:
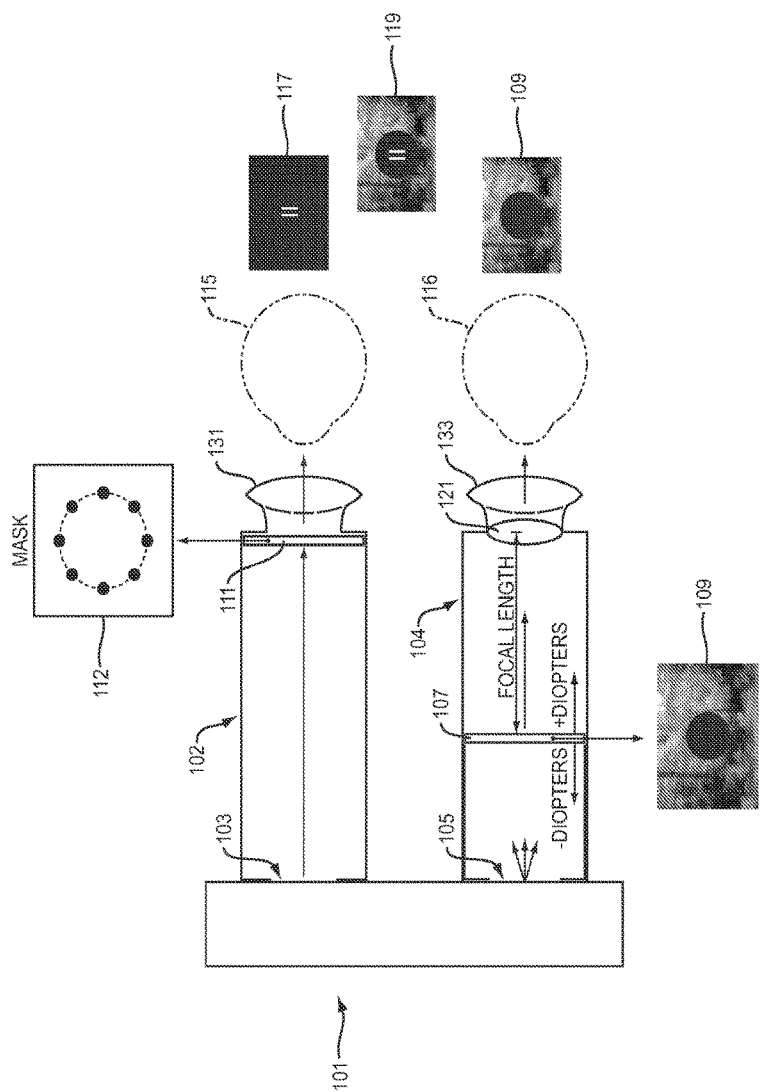
FIG. 1 is a cross-sectional schematic of a bi-ocular apparatus for relaxing one eye while measuring refractive aberration of the other eye.

FIG. 1 shows an example of a bi-ocular apparatus, in which a lens 121 and film 107 are used to present stimuli to an idle eye 116 while refractive aberration of a test eye 115 is being measured. A display device (e.g., cellphone) 101 includes a screen region 103 for displaying a test optical pattern. Light from that pattern travels through a mask 111 to the test eye 115. An example of such a mask, which is shown in side view at 111 and in front view at 112, comprises a pinhole mask. A mask 111 may be dynamically modifiable. For example: (a) mask 111 may be dynamically modified to cause images (e.g., two dashed lines) perceived by the subject to align; and (ii) the particular modification of the mask needed to achieve this alignment may be mapped to a particular type and degree of refractive aberration.

The display device also includes a screen region 105 for displaying an optical pattern that backlights the film 107. The backlit film 107 displays a relaxation image 109. The relaxation image 109 is presented to the idle eye 116 while the test image is presented to the test eye 115.

When both eyes are open, the subject perceives a combined image 119, in which the relaxation image appears to surround the test image. When viewing the device, a subject can press his eye sockets against eye cups 131, 133.

In some implementations, the distance between film 107 and lens 121 can be adjusted, in order to control relaxation of the idle eye. For example, the distance between the film 107 and lens 121 (the "lens/film distance") may be adjusted as follows: (i) subject puts the device very close to the eye(s); (ii) the lens/film distance is increased up to the point the relaxation image 109 appears blurred; (iii) the lens/film distance is decreased up to the point that the relaxation image 109 appears in focus; (iv) the lens/film distance is increased up to the point the relaxation image 109 appears blurred; and (v) refractive aberration of the test eye is measured while the relaxation stimuli continues to be presented to the idle eye.

The lens/film distance can be adjusted by: (a) moving the film 107, (b) moving the lens 121, or (c) moving both the film 107 and the lens 121. For example, in some implementations, the film 107 can be moved relative to the main body of optical channel 104, but the position of the lens 121 is fixed relative to that main body. In other implementations, the lens 121 can be moved relative to the main body of optical channel 104, while the position of the film 107 is fixed relative to that main body.

Figure 2:
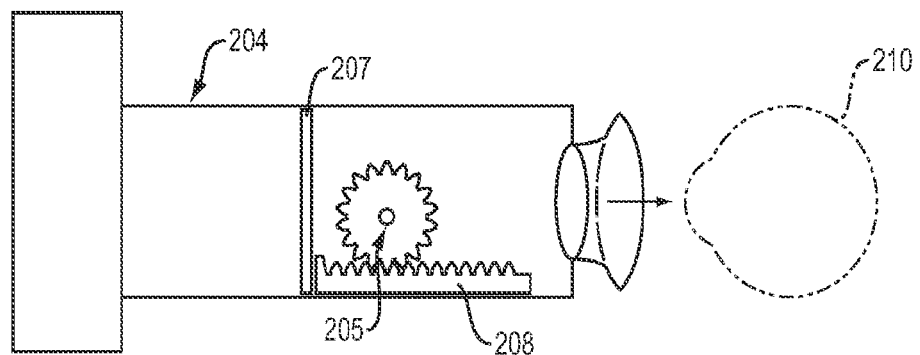
FIG. 2 is a cross-sectional schematic that shows a mechanism for translating a film.

The movement of the film 107 or lens 121 (as the case may be), may be powered by a human. For example, a human may move a part of the apparatus, and motion of that part may be mechanically translated into linear motion of the film 107 or lens 121 (as the case may be). The human may be (i) a subject who is taking a refractive aberration test with the apparatus, or (ii) a person who is administering a refractive aberration test to a subject. FIG. 2 shows an example of a mechanism for transforming human motion into linear motion of a film 207. A human can turn a knob, thereby rotating a shaft 205. A rack and pinion system 208 translates the rotational motion of the shaft 205 into linear motion of the film 207. Alternately, a rack and pinion system can translate rotational motion imparted by a human into linear motion of lens 121. Alternately, movement of the film 107 or lens 121 can be actuated by electronically-controlled motors.

In some implementations of this invention, lens 121 is an adaptive lens. In that case, the lens/film distance need not be actually changed. Instead, a similar effect may be achieved by changing the shape (power) of the adaptive lens 121. Thickening the adaptive lens (increasing its power, decreasing its focal length) has the same effect as increasing the lens/film distance; whereas thinning the adaptive lens (decreasing its power, increasing its focal length) has the same effect as decreasing the lens/film distance. For example, adaptive lens 121 may comprise: (i) a liquid lens that can increase and decrease power by changing the amount of liquid inside; (ii) an electrowetting lenses which can change the surface tension of liquids to produce a desired lens curvature and thus optical power; (iii) an electroactive lens which can change the refractive index of liquid crystals inside the lens, changing the lens' power; (iv) Alvarez lenses which slide on top of each other to produce a desired optical power; or (v) an adaptive optics device (such as an array of deformable mirrors, MEMs) which can create the given optical power via software.

Figure 3:
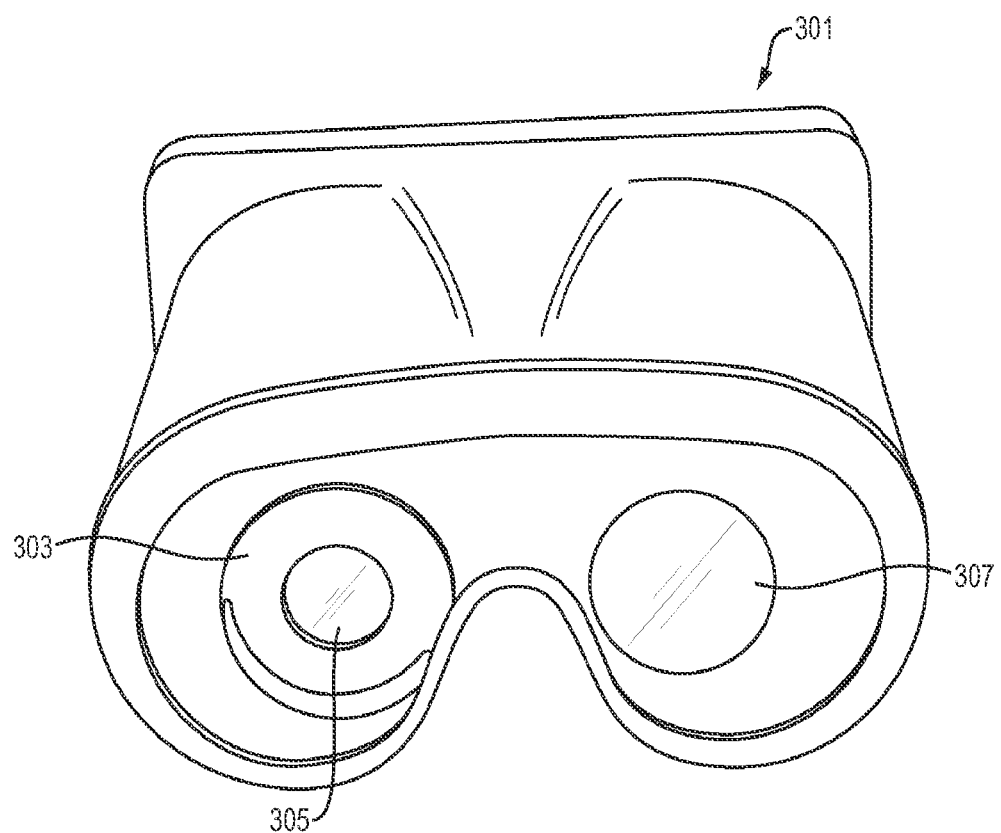
FIG. 3 is a perspective view of a bi-ocular apparatus with a lens holder for a replaceable lens at the "viewing end" of an optical channel.

In some implementations of this invention, an extra, replaceable lens (in addition to lens 121) is placed along the optical path between the film 107 and the idle eye 116. For example, the extra lens may be either optically closer to (or optically further from) the idle eye 116 than lens 121. In implementations with such an extra, replaceable lens, the lens/film distance need not be actually changed. Instead, a similar effect may be achieved by changing the power of the extra, replaceable lens (e.g., by removing a lens with one power and replacing it with a lens of another power). For example, (a) an extra lens with positive power moves the point on which the subject is focusing farther away from the eye; and (b) an extra lens with negative power moves the point of focus closer. FIG. 3 shows an example of a bi-ocular device 301 with an extra, replaceable lens 305 supported by a lens holder 303. Depending on the particular implementation, the lens holder may releasably support only one replaceable lens for one eye, or the lens holder may releasably support two lenses, one for each eye. In the example shown in FIG. 3, the lens holder only supports a lens for the optical channel on the left, and not a lens for the optical channel 307 on the right. The lens holder's shape and material properties allow a lens to be easily inserted and removed from the lens holder. In some implementations, an extra, replaceable lens is repeatedly replaced during a relaxation/testing procedure by lens of different optical powers.

For example, an extra, replaceable lens may be used as follows: The subject starts by choosing the strongest replaceable lens in which he still sees images in focus. In this case, the overall test may be taken in a few rounds over the following procedure: (i) the subject takes the test; (ii) the subject or a technician checks the spherical result measured in the test and adds 1 or 2 diopters to the measured spherical power; and (iii) a lens 305 with the computed refractive power is then slid into the lens holder 303 in the front of the idle eye and the procedure starts again. The test finishes when there is no difference in the spherical power needed on the relaxation lenses from a previous result to the current one. This procedure may be varied, depending on the particular implementation.

In some implementations of this invention, the actual and apparent lens/film distance is simply kept steady throughout testing of a subject. In that case, change in the lens/film distance neither occurs physically, nor is it emulated (e.g. by adaptive lens or an extra, replaceable lens).

Even when the actual and apparent lens/film distance is kept steady, the apparatus can be used to control relaxation (accommodation) of the eye. In that case, the constant lens/film distance determines the conditions or range of optical powers the device is able to measure. For example, the lens/film distance may be substantially equal to one focal length of lens 121. This makes the subject's eye relax towards infinity. Myopes cannot focus at infinity but the infinity stimuli makes them relax their lens to the closest point to infinity, creating a favorable point for the measurement. Hyperopes require the film 107 to be more than one focal length away from the lens 121, creating a stimulus beyond infinity.

More generally, in the steady distance case, the range of powers which the device can support depends on the lens/film distance. The eye relaxation happens in subjects that need correction (q in diopters) from −20 to q, where $q=1/f-1/d$, f is the focal length of lens 121, and d is a fixed distance from film 107 to lens 121. For example, if d equals to f, the image is virtually at infinity and the device works for all myopic individuals (−20 to 0D). If d is bigger than f, hyperopes can be measured. The equation $q=1/f-1/d$ is the same for all devices, having moving parts or not.

In alternate implementations, a constant distance between lens 121 and a surface displaying the relaxation image can be achieved without using a backlit film 107. For example, backlit film 107 can be omitted, and screen region 105 can instead display the relaxation image 109. In that case, the constant distance between screen region 105 and lens 121 is analogous to the constant lens/film distance discussed above. In this setup, the screen plays a similar role to that of the film 107 described above.

Figure 4:
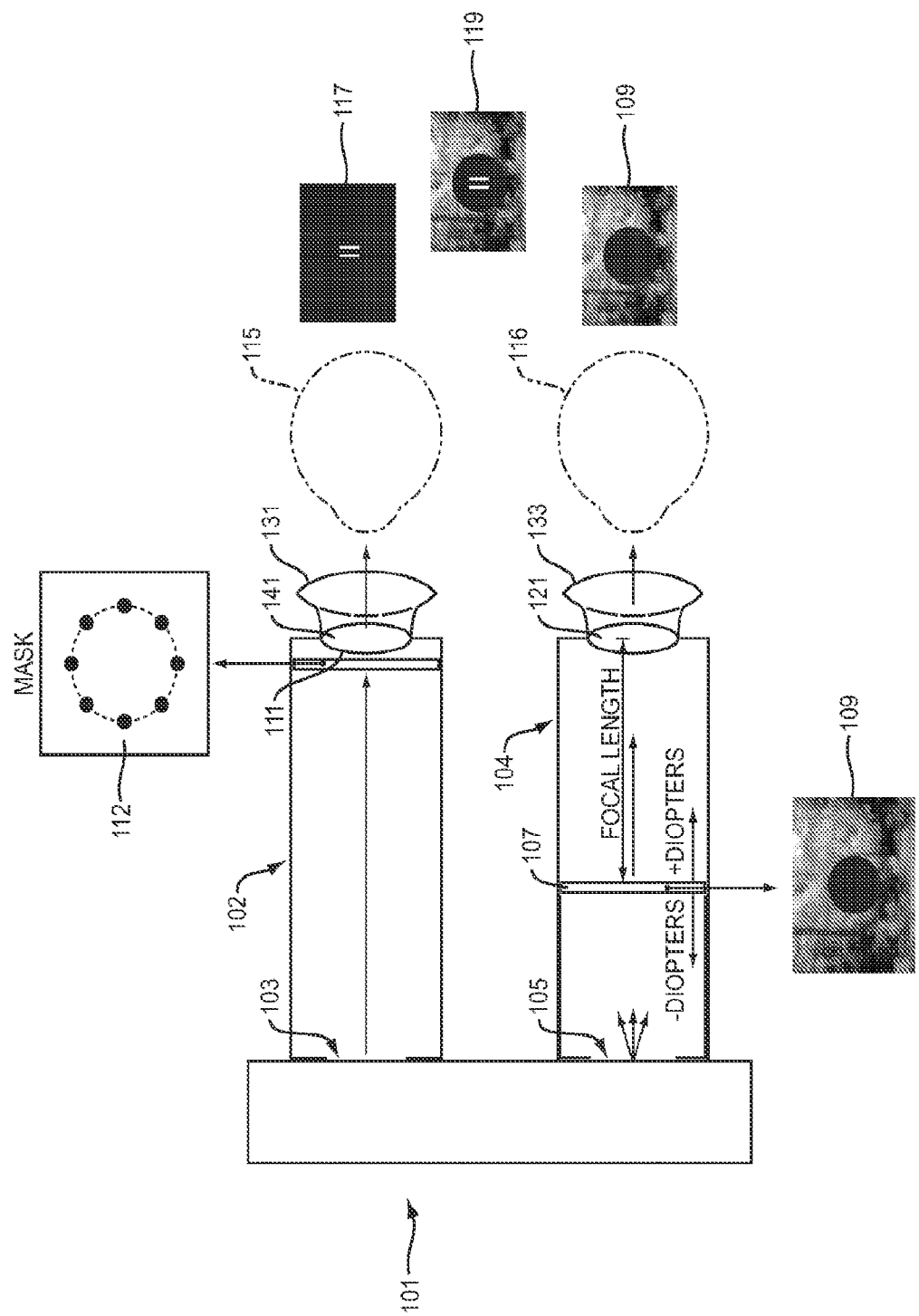
FIG. 4 is a cross-sectional schematic of a bi-ocular apparatus with relaxation lenses for both eyes.

In some implementations, a bi-ocular apparatus uses lens for both eyes, and more particularly: (a) a lens and film in the optical channel for the idle eye, and (b) a lens in the optical channel for the test eye. FIG. 4 shows an example of such a configuration. FIG. 4 is identical to FIG. 1, except for the addition of second lens 141. Lens 141 is positioned in an optical path between mask 111 and test eye 115. Lens 141 alters the apparent position of the test image displayed by mask 111, compared to the apparent position of the test image in the absence of lens 141. Lens 141 can make the subject's eyes relax while the subject takes a refractive aberration test as well as create a similar stimulus for convergence. Alternately, rather than use an image displayed by film 107, an image displayed by a screen region (e.g. 103) may be used. In that alternate case, film 107 is omitted.

Fiber-Optics:

In some implementations of this invention, optical fibers are used to control eye relaxation. A subject looks into the display at close range, focuses on the fibers, or on the image created by the fibers, and performs the test.

Figure 5:
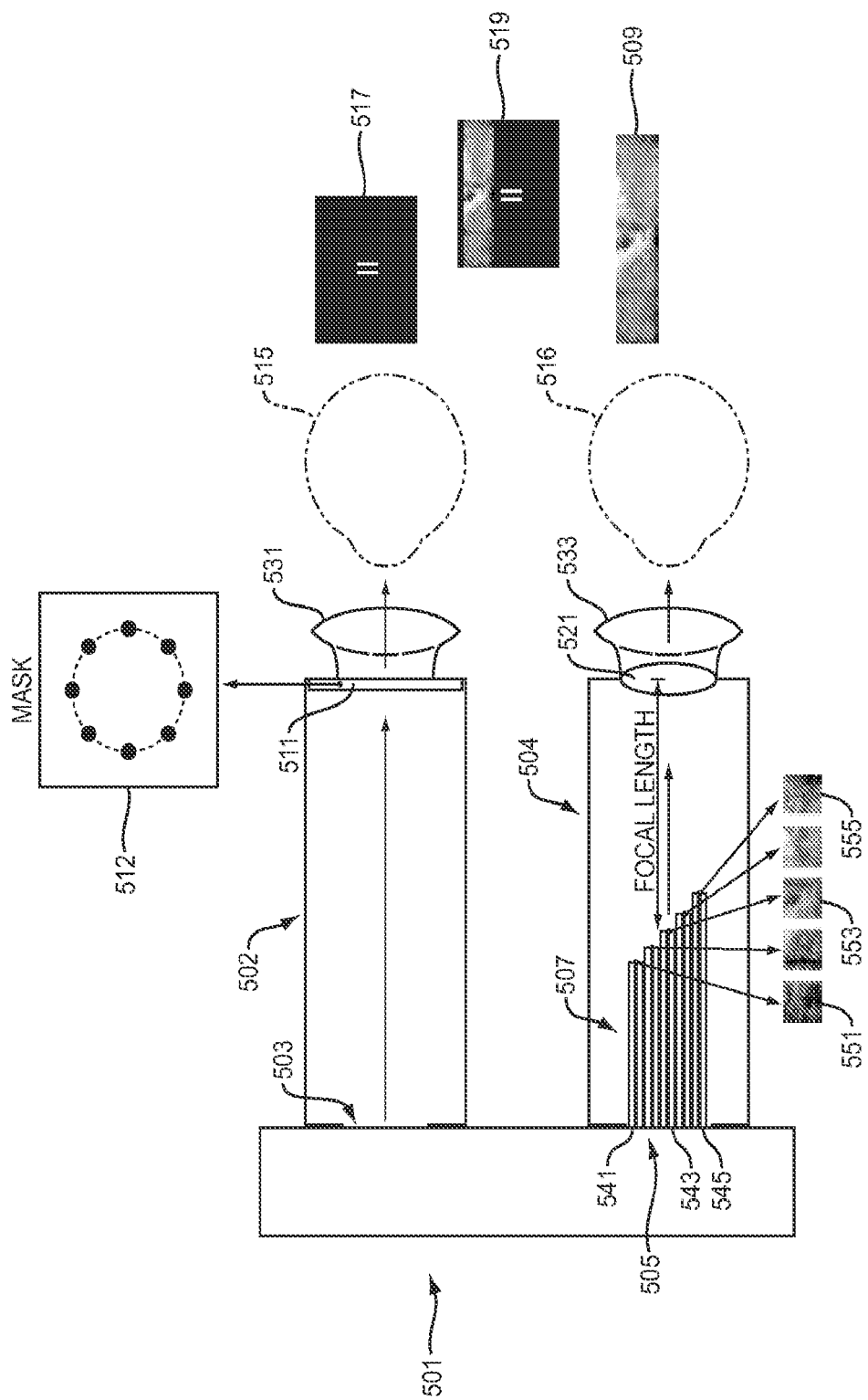
FIG. 5 is a cross-sectional schematic of a bi-ocular apparatus that includes optical fibers for presenting stimuli to relax an eye.

In the example shown in FIG. 5: A display device 501 includes a screen region 505 that displays a pattern to illuminate optical fibers. The optical fibers 507 are divided in clusters that have a given length such that each cluster creates a light source in a different optical depth. Each cluster contains one or more fibers. Each cluster of fibers, respectively, creates an illusion of an object at a different depth from the eye. At one end of the fiber bundles, the fiber bundles touch or are adjacent to screen region 505. As different pixels of screen region 505 are turned on and off, distinct fiber depths are illuminated, which activates and deactivates given depths during the test. Only one fiber bundle is turned on at a time. Different films (e.g., 551, 553, 555) may be positioned at the tips of optical fibers. The subject will focus on the tip of the bundle that is being illuminated by the display device (e.g., cellphone) 501.

The fiber optic bundles 507 may terminate at varying distances from lens 521 which are all close to a focal length of lens 521. A software program controls when different parts of screen region 505 are illuminated. As different parts (e.g., 541, 543, 545) of screen region 505 are illuminated, different fiber optic bundles are illuminated. Each cluster of optical fibers terminates at a different depth from lens 521. One or more fibers are placed for each depth, forming a cluster. Each cluster is activated to create a visual stimulus for a desired depth. When a cluster ends exactly at the focal length of lens 521, that cluster is generating a stimulus of an object at infinity.

As the subject starts the test, the screen region 505 illuminates the fiber optic cluster that terminates optically closest to the idle eye 516. Via an interactive procedure, the subject changes the illuminating cluster (e.g., by pressing buttons on the phone), from optically closer to optically farther from the eye up to the point he cannot sharply focus anymore. To change the illuminating cluster, software running on the phone turns on and off regions on the screen that have been previously calibrated for given clusters. In this implementation, at the macro-scale, no optical component in the apparatus moves relative to the rest of the apparatus.

Fibers from many clusters can be mixed on the extremity close to the eye to enhance the visual stimulus. Also, the fibers can be placed in such a way that a bundle creates an apparent pattern on both the left and right sides of the relaxation image. If the distribution of a cluster's fibers is irregular close to screen region 505, a software calibration procedure may map for each pixel on screen, the depth that is being activated.

The calibration is an imaging procedure that correlates which pixels are highlighting which fibers. It can be done with a simple webcam focusing at infinity or at the fiber's tips. An image-processing algorithm finds the highlighted depths and stores into a table while changes the active pixels on the screen.

Fibers can be positioned in cluster mode with films (e.g., 551, 553, 555) at the tips, or fibers can be mixed to increase the feeling of depth, or fibers can be positioned in such a way that they start in clusters on the screen and end mixed or in a different distribution on the other extremity.

Figure 6:
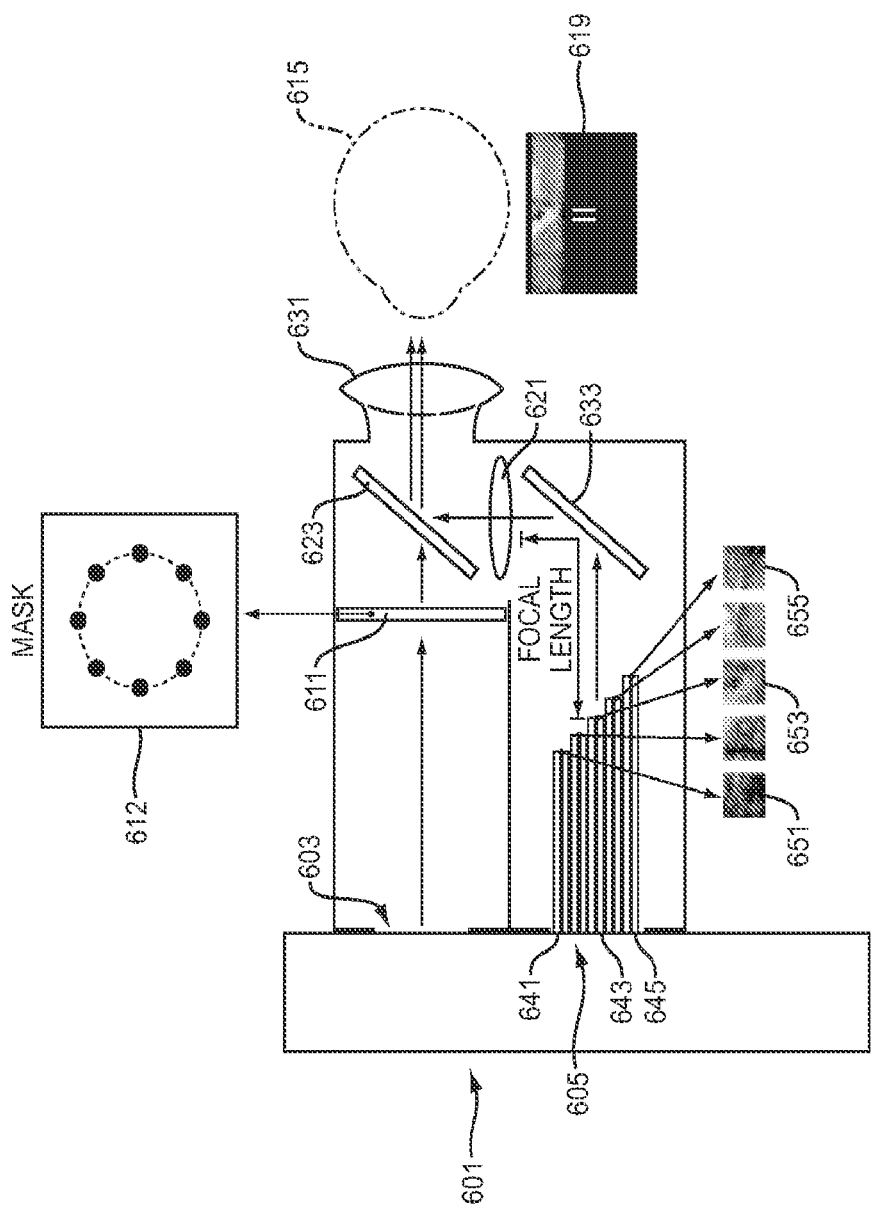
FIG. 6 is a cross-sectional schematic of a monocular apparatus that includes optical fibers for presenting stimuli to relax an eye.

In alternative embodiments of this invention, a monocular apparatus, instead of a bi-ocular apparatus, includes optical fibers for presenting relaxation stimuli to an eye. FIG. 6 shows an example of such a monocular apparatus 601. In the example shown in FIG. 6, relaxation stimuli are delivered to eye 615 via a mirror 633, a lens 621, and a beam splitter 623. Likewise, test stimuli are transmitted through the beam splitter 623 to the eye 615. In this implementation, at the macro-scale, no optical component in the apparatus moves relative to the rest of the apparatus. Alternately, this strategy (beamsplitters, mirrors and optionally optical fibers) may be employed in a bi-ocular device that has testing and relaxation features for both eyes and uses convergence to strength the relaxation stimulus.

In the fiber optic examples shown in FIGS. 5 and 6, the following test procedure can be used. In the first part of the test, a subject looks through the device and adjusts the device to the maximum distance at which he can see the fibers or the film on top of them (e.g., 551, 553, 555, 651, 653, 655) in sharp focus. The device lights up pixels on screen region 505, 605 representing each depth the subject is seeing, one at a time. In the latter part of the test, software runs the eye test. To find the maximum distance, the software illuminates clusters with given depths from close to far. Throughout this process, the viewer's eye is focused as far as possible (relaxed state).

Figure 11:
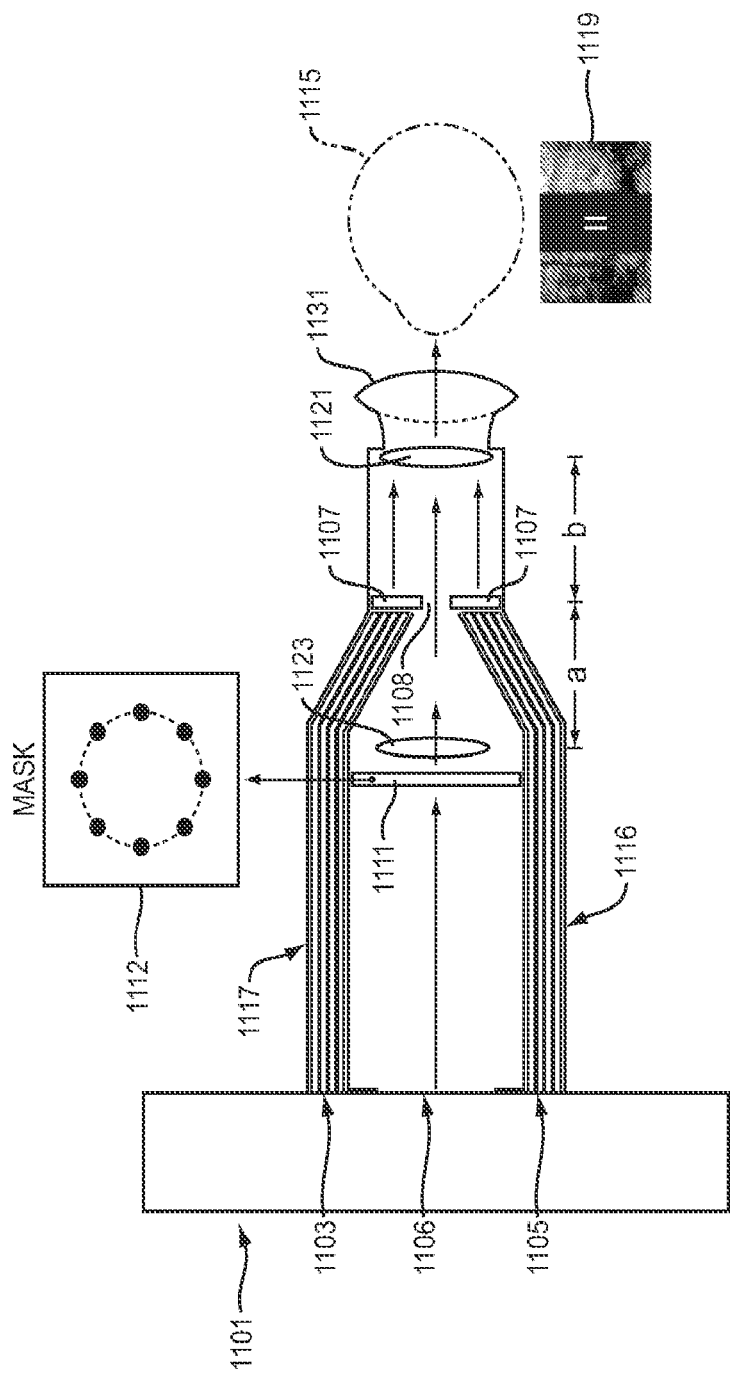
FIG. 11 is a cross-sectional schematic of a monocular apparatus with a 2f optical system.

In some implementations of this invention, monocular apparatus with a 2f optical configuration uses fiber optics to help control relaxation of an eye. An example of such a configuration is shown in FIG. 11. A film 1107 displays a relaxation image. The film 1107 is backlit by optical fibers (1116, 1117), which are in turn illuminated by screen regions 1103, 1105. Optionally, optical fibers 1116, 1117 can be omitted, and film 1107 can be directly backlit by screen regions 1103, 1105. However, the optical fibers are preferable because the illumination of film 107 is brighter when optical fibers are used than when optical fibers are omitted.

In the 2f configuration shown in FIG. 11, lens 1123 and lens 1121 each have the same focal length, and are positioned 2 focal lengths away from each other. Film 1107 can be positioned midway between the two lenses (i.e., one focal length from lens 1123 and one focal length from lens 1121. The backlit film 1107 displays a relaxation image that appears to the subject to be far away (e.g., at or close to infinity distance). Depending on the particular implementation, film 1107 may be backlit (i) by screen regions (e.g., 1103, 1105) via optical fibers or (ii) by ambient light from the outside world through an opening in the device. Film 1107 can have a hole or a non-attenuating material in a central region 1108 of the film, so that the light which comes from a display screen (e.g., 1106) and passes through this central portion 1108 does not get attenuated.

Film 1107 can be moved back and forth, thereby changing distances a and b, where a is the distance between film 1107 and lens 1123, and b is the distance between film 1107 and lens 1121. Moving film 1107 back and forth causes the apparent depth of the relaxation image displayed by film 1107 to vary, and thus can be used to relax the eyes. If b is equal to the focal length of 1121, the viewing eye receives a stimulus at infinity. If b is bigger than the focal length of 1121, the stimulus is placed optically beyond infinity. Since the testing optical channel is not affected by the position of the film, due to the hole in the center of 1107, the test procedure does not change . . . .

The diameter of the pattern in the mask 1112 is limited by the pupil diameter of the viewer, which can be from 2 mm to 9 mm. If the mask is bigger than the pupil diameter, the iris will occlude part of the testing channel light rays and the measurement fails. Changing the focal length of 1108 and 1121 independently allows for optical magnifications of the mask and the usage of bigger patterns to increase resolution while optically reducing the patterns to the subject's pupil size. The ratio between the focal lengths is proportional to the magnification of the testing patterns.

In some implementations, the film (e.g., 107, 1107) which displays the relaxation image can be moved perpendicular to the optical axis of the optical channel that presents relaxation. This perpendicular movement can compensate for prismatic effects and thus avoid convergence.

Movement of film 1107 can be powered by a human, via a mechanism that transforms movement by a human into linear translation of the film. Or, linear translation of film 1107 may be actuated by electronically-controlled motors.

The embodiments shown in FIGS. 1, 2, 5, 6, 7, 8, 10, 11, 15, 21 have some similarities to each other. Among other things: A display device (e.g., cellphone) 101, 501, 601, 701, 1001, 1101, 2101 may include a screen region 103, 503, 603, 703, 1003, 1103, 2103 for displaying a test optical pattern. Light from that test pattern may travel through a mask 111, 511, 611, 711, 1011, 1111, 2111 to an eye 115, 515, 615, 715, 1015, 1115, 2115. For example, masks are shown in side view (actual position) at 111, 511, 611, 711, 1011, 1111, 2111 and in front view (for clarity of presentation) at 112, 512, 612, 712, 1012, 1112, 2112. These masks are not limited to pinhole masks, but may instead be of any type. A mask (e.g., 111, 511, 611, 711, 1011, 1111, 2111) may be dynamically modifiable. For example: (a) a mask (e.g., 111, 511, 611, 711, 1011, 1111, 2111) may be dynamically modified to cause images (e.g., two dashed lines) perceived by the subject to align; and (b) the particular modification of the mask needed to achieve this alignment may be mapped to a particular type and degree of refractive aberration. If the apparatus is bi-ocular, a relaxation image (e.g. 109, 509, 710, 1055) may be presented through a lens 121, 521, 721, 1021, to one eye 116, 210, 516, 716, 1016, 2116 while a test image (e.g., 117, 517, 717, 1017) is presented to the other eye 115, 515, 715, 1015, 2115. Or, for example, light from screen regions may pass through two lenses, one for each eye 1521, 1523, before reaching both eyes. When both eyes are open, the subject may perceive a combined image 119, 519, 719, 919, 1019,

1011 in which the relaxation image appears to surround the test image. If the apparatus is monocular, a relaxation image and a test image may be presented through a lens 621, 1121 to the same eye 615, 1115. The subject may perceive a combined image 619, 1119. A user may press his face against a pair of eyecups (e.g., pair 531, 533, pair 731, 733, pair 931, 933, pair 1031, 1033, pair 1531, 1533, or pair 2131, 2133) if the apparatus is bi-ocular, or against an eye cup 631, 1131 if the apparatus is monocular. The apparatus may include a first optical channel 102, 502, 702, 1002, 1502, 2102 and a second optical channel 104, 204, 504, 704, 1004, 1504, 2104.

Progressive Lens:

In some implementations of this invention, a progressive lens is used to relax the eye.

Figure 7:
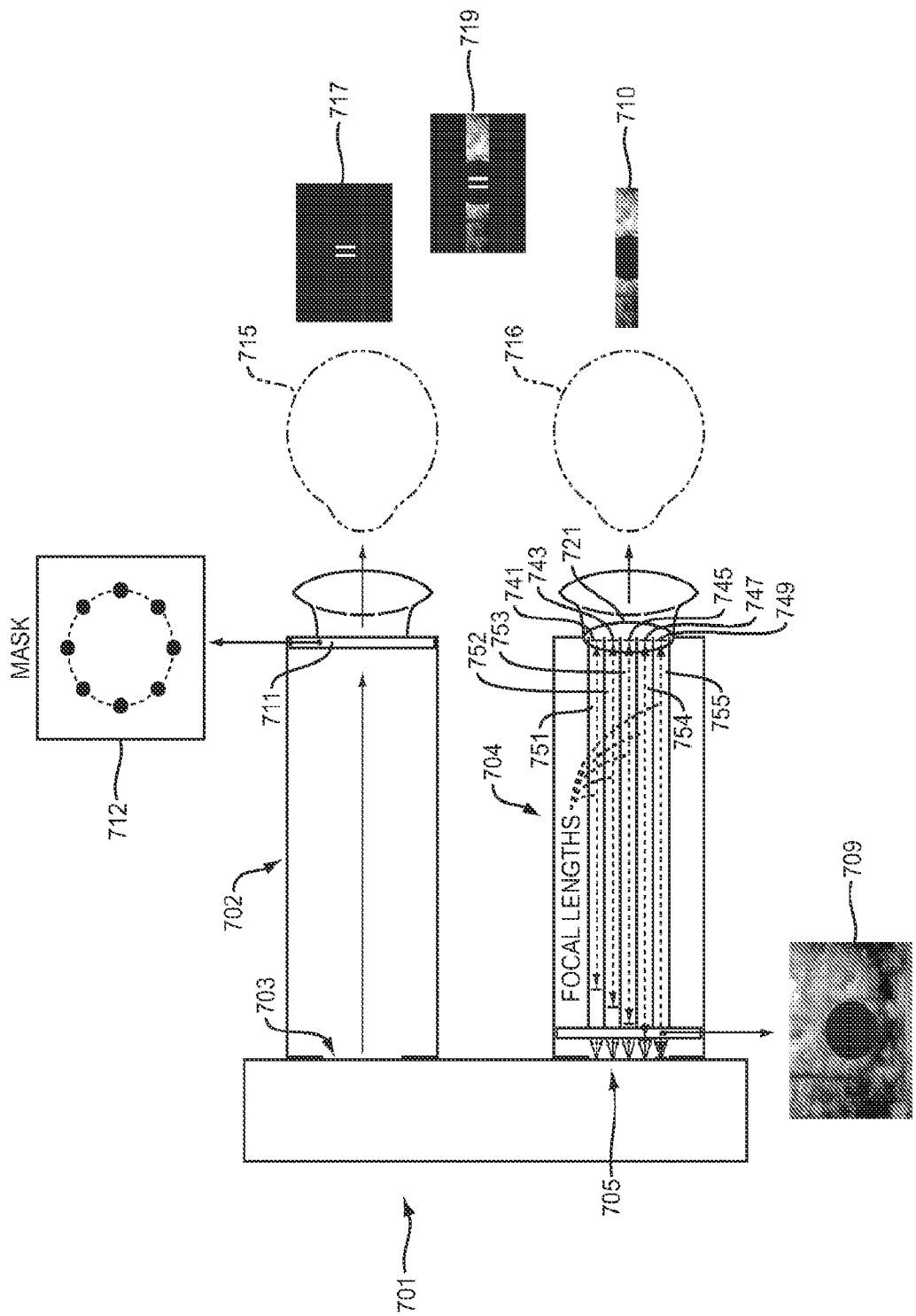
FIG. 7 is a cross-sectional schematic of a bi-ocular apparatus that includes a progressive lens and blockers to allow the selection of one sector of the lens at a time via software.

FIG. 7 shows a bi-ocular example of such a configuration. In this example, at the macro-scale, no optical component in the apparatus moves relative to the rest of the apparatus. Instead, screen region 705 emits an optical pattern that backlights film 707, causing film 707 to display a relaxation image 709. Different parts (e.g. 741, 743, 745, 747, 749) of a progressive lens 721 have different powers. As a result, different areas of relaxation image 709, when viewed through different portions of progressive lens 721, appear to be at different depths from the subject. Each area of film 707 (and the relaxation image 709 that the film displays) produces a given depth illusion. Thus, by viewing relaxation image 709 illuminated by screen region 705 through different parts of progressive lens 721 at different times, the apparent depth of image 709 can be changed. The subject focuses on the illuminated depth. Preferably, a set of blockers 751, 752, 753, 754, 755 selectively occludes light from film 707, thereby preventing light from parts of film 707 from reaching a non-desired part of progressive lens 721. If the power of the progressive lens varies spatially in discrete steps from one area to another area of the progressive lens, then the size and number of blockers can be same as the size and number of these areas.

Depending on the particular implementation, different patterns may be used in the progressive lens 721. For example, optical power of a progressive lens 721 may vary uniformly or in discrete steps in (a) a spatial pattern comprising concentric circles, or (b) a pattern with straight, parallel lines, where optical power is spatially constant along each respective straight, parallel line.

In some implementations, film 709 is omitted. In that case, a relaxation image can be displayed by screen region 705, rather than by film 709. The choice of using film or the direct screen is dependent on the required resolution of the system (which is a function of its size and lens powers). Advantageously, film may have a higher resolution than a display screen. For example, film printed by a popular film printer may have higher resolution (e.g., 5000 DPI) than popular electronic screens (e.g., 400 DPI).

In the example shown in FIG. 7, a test of refractive aberration may be performed in two rounds. First, in a calibration process, different parts of film 707 are illuminated (or unblocked by blockers). Each part renders a stimulus at a different depth. The parts are sequentially illuminated (or unblocked by blockers), from the closest stimulus to the farthest. Subject stops and presses a button to indicate when he sees the first slightly blurred image. With the accommodation calibrated, the subject takes a refractive aberration test. Alternatively, another human (e.g., a technician) can help the subject find the first slightly blurred image.

Figure 8:
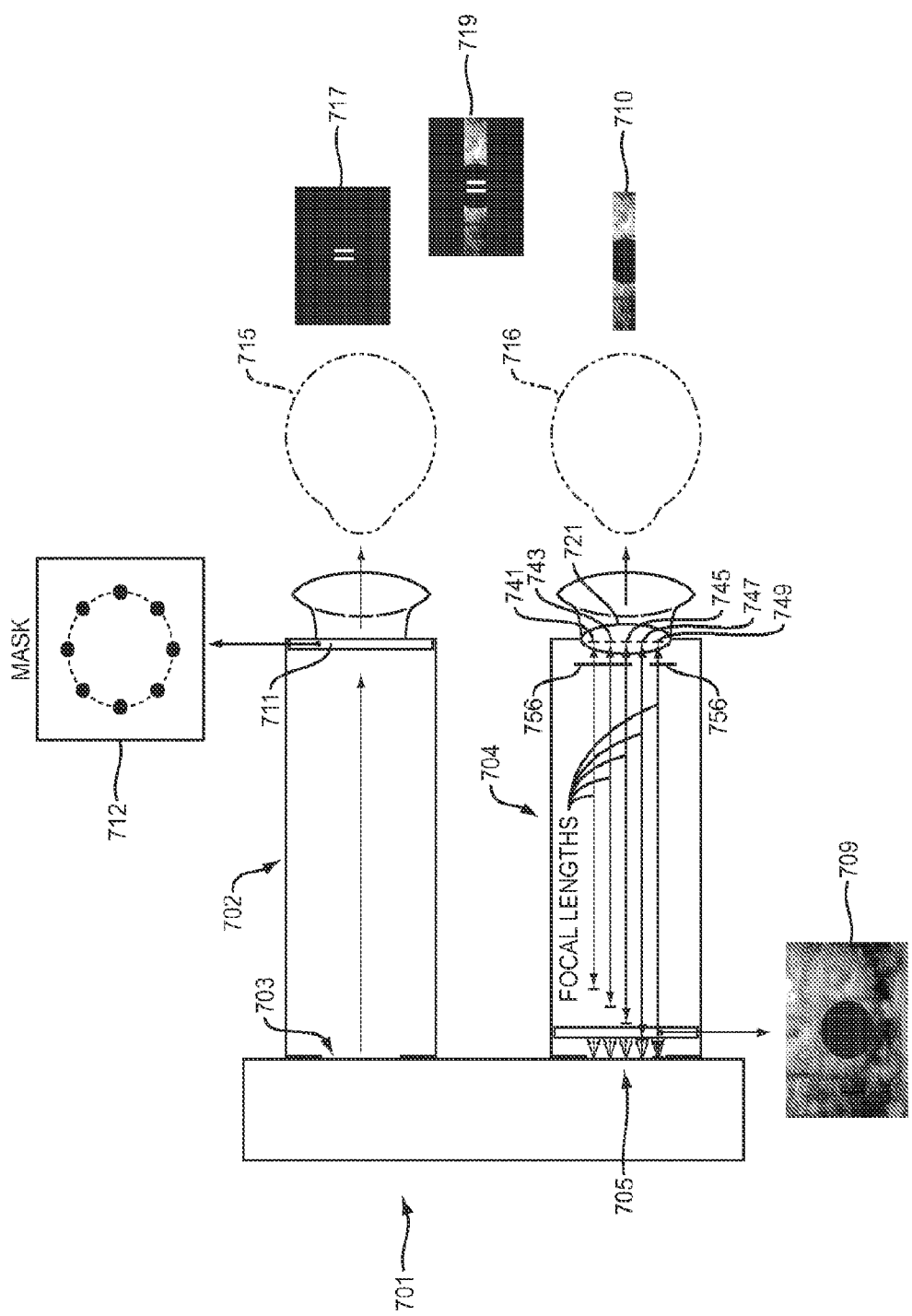
FIG. 8 is a cross-sectional schematic of a bi-ocular apparatus that includes a progressive lens and a manually or electronically actuated sliding blocker.

Alternatively the blockers may comprise a slideable barrier 756 close to the progressive lens 721, as shown in FIG. 8. In the example shown in FIG. 8, the slideable blocker barrier 756 can be moved up and down to allow the subject to choose the sharpest position before seeing a blur image. In this setup, the eye relaxation procedure can be: (i) the subject puts the device very close to the eye; (ii) the slideable barrier 756 is moved up to the point the image becomes blurred; (ii) the slideable barrier 756 is moved back up to the point the image is in focus again; (iii) the slideable barrier 756 is moved up to the point the image is slightly blurred again; and (iv) subject takes the vision test. Alternatively, another human (e.g., a technician) can move the blockers (or cause them to be moved), and then the subject indicates whether he sees the image clearly.

In the examples shown in FIGS. 7 and 8, the calibration process can be controlled by any conventional means, including (a) a human rotating a knob that is attached to a motion transmission mechanism to mechanically adjust the blockers, or (b) by software-controlled electronics which control mechanical movement of the blockers or which control other spatially varying occlusion by the blockers.

A progressive lens may be used in either a monocular apparatus (e.g., with beam splitters) or in a bi-ocular apparatus.

Figure 9:
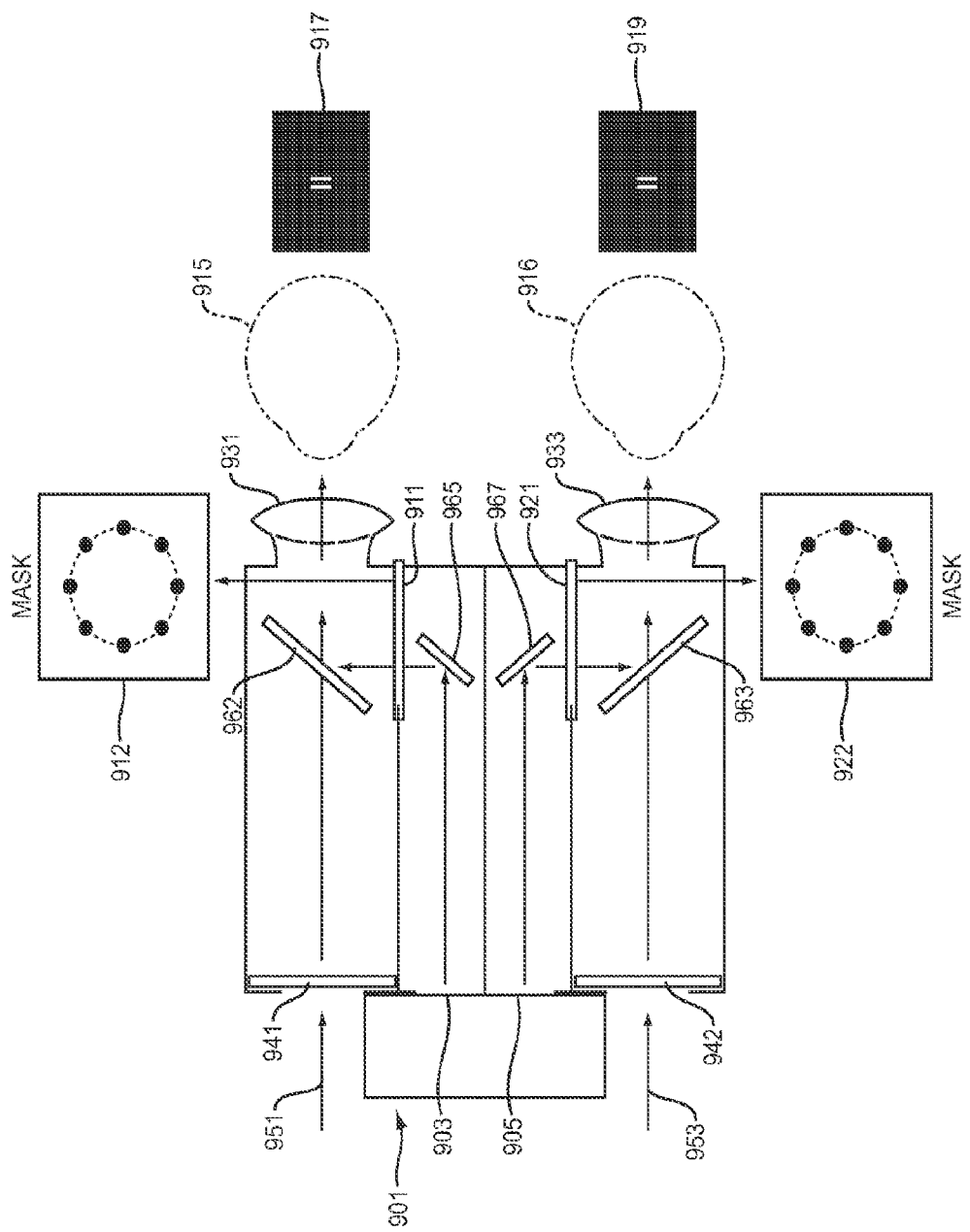
FIG. 9 is a cross-sectional schematic of a bi-ocular apparatus for presenting an open view of an external environment to an idle eye while measuring a test eye.

Open View:

FIG. 9 shows an example of an open-view apparatus for relaxing one eye while refractive aberration of a second eye are being measured. In this example, the apparatus is pointed so that optical axes 951 and 953 focus at a far distance on the external, real world. A display device (e.g., a cell phone) 901 is positioned so that the display in screen regions 903, 905 (and the view of the external world along axes 951 and 953) are not occluded by the subject's nose. (For example, the display device screen can be oriented in "portrait" and aligned with the subject's nose.) Screen regions 903, 905 can display test images 917, 919, one for each eye. Preferably, however, only one eye is tested at a time. Polarizers 941, 942 decrease the light intensity of the external world, making the subject able to see the patterns of the test image. For each eye, respectively, a mirror 965, 967, a mask 911, 921 and a mostly reflective beam splitter 962, 963 lie in the optical path from the screen region 903, 905 to the subject's eye 915, 916. Examples of the masks, which are shown in side view at 911, 921 and in front view at 912, 922, each comprise a pinhole mask. The mask 911, 921 may be dynamically modifiable. When viewing the device, a subject can press his eye sockets against a pair of eye cups 931, 933. The user perceives the test image superimposed on a relatively dim view of a distant object in the real world. Any one or more of the masks (911, 921) may display, when illuminated, a pre-computed pattern.

3D Image:

In some implementations of this invention, an apparatus displays a virtual 3D image at an apparently varying depth, thereby controlling relaxation of an eye. A software-controlled display can make the 3D virtual object appear to move closer to or farther from the subject, or to come in and out of focus at different virtual depths.

Figure 10:
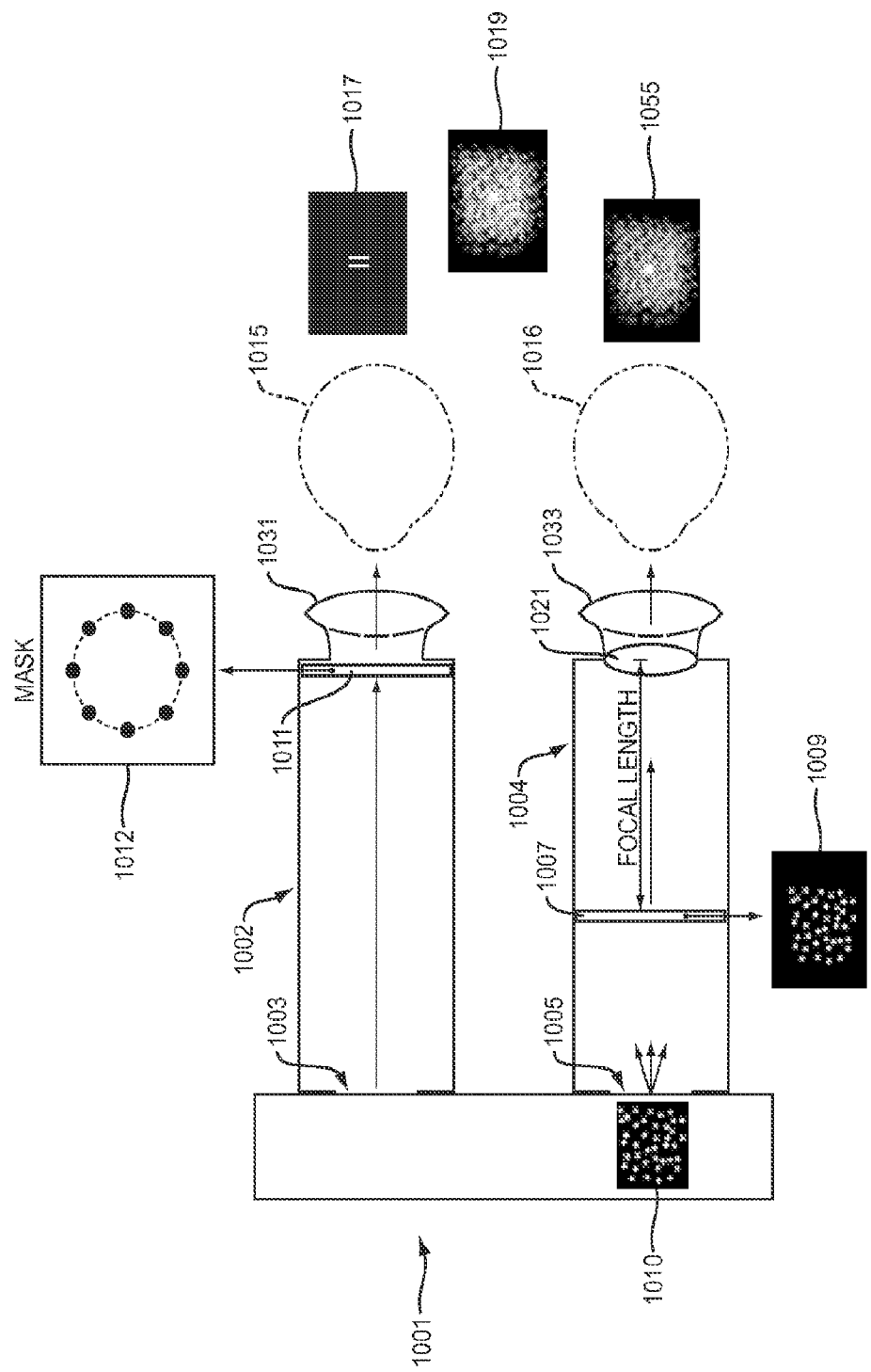
FIG. 10 is a cross-sectional schematic of a bi-ocular apparatus for displaying a 3D image to relax an idle eye while measuring a test eye.

FIG. 10 shows an example of such an apparatus. In this example, a virtual 3D image is displayed to the idle eye at an apparently varying distance from the idle eye. Screen region 1005 displays image 1010. A film 1007 acts as a mask 1009 to filter image 1010. If the pattern of image 1010 and the pattern of mask 1009 are the same, then software can apply a scale to image 1010 to change the apparent depth of the virtual object. As the scale of image 1010 increases, the subject focuses farther. Image 1010 and mask 2009 may, but are not necessarily, precomputed for different depths.

In the example shown in FIG. 10, the test may be an interactive, computer-controlled process as follows: (i) the subject sees only the virtual 3D image; (ii) the apparent depth of the virtual 3D image is increased up to the point the image disappears; (iii) the apparent depth of the virtual 3D image is decreased back to a previous stage where the subject still see the image; and (iv) subject takes a refractive aberration test on the test eye.

Given a regularly spaced pinhole mask, a computation may relax the constraint of regularly spaced pinholes by jittering each pinhole by a small amount. The correspondingly pattern behind each pinhole in the display may also be jittered. The jittered pattern converts the crosstalk between pinholes into random noise. Given a desired pattern to be shown to the idle eye 1016 and a jittered pin-hole array 1009, placed at distance (f) from pattern 1010, the pattern 1010 is obtained by convolution, (H)=A×L, where x is a convolution operator. For example, if pattern 1010 is a pinhole pattern, the scaling on pattern 1010 to create virtual objects at given depths may be a multiple of shift c (as defined herein)

FIG. 21 is a conceptual sketch that shows two masks (mask 2109 and mask 2110) creating a virtual 3D object. In this example, mask 2109 is a scaled version of mask 2110. Scaling mask 2109 or mask 2110 moves the virtual object closer or further to the lens. In this example, light rays from mask 2110 pass through mask 2109 and intersect at point 2145, before the light reaches lens 2121 and eye 2116. FIG. 21 is over simplistic, e.g., it does not account for cross-talk between the pinholes.

(In the attached Figures, all masks are actually perpendicular to the longitudinal axis of their respective optical channels, rather than in plane with the Figures. For example, masks shown in FIG. 21 are actually perpendicular to the longitudinal axes of optical channels 2104 and 2102, rather than in plane with FIG. 21 as shown. Mask 2110 is at position 2105; Mask 2109 is at position 2107.)

Alternately, the virtual 3D image used to relax an eye may be created in other ways, including tailoring. More generally, any method that creates a light field to display a virtual object at different points in space may be employed. Given as input an expected image to be received by the retina of the subject's eye, the method produces a light field to be shown on a specified display. For example, the method can be performed in two main steps: (i) pairing individual light-field rays (e.g., rays generated from a double stack of LCDs) and retinal positions to associate a raw intensity to each ray; and (ii) normalizing retinal "pixels". This approach can be described as the projection of depth-dependent anisotropic patterns that may account for the spatially-distributed optical aberrations of the eye that is being measured. The depth-dependent patterns are anisotropic images (as defined herein) virtually placed at the right point in focus for a given optical power. The result is a light field that displays one or more virtual 3D objects at given distances from the eye. The apparent depth of an anistropic image can serve as a visual cue to induce the subject to focus at that depth.

Mask:

In exemplary implementations of this invention, light passes through a mask before reaching a test eye. The mask may be dynamically reconfigurable. For example: (a) a mask (e.g., 111, 511, 611, 711, 1011, 1111, 2111) may be dynamically modified to cause images (e.g., two dashed lines) perceived by the subject to align; and (b) the particular modification of the mask needed to achieve this alignment may be mapped to a particular type and degree of refractive aberration. A mask may, but does not necessarily, have a spatial pattern described in the NETRA patent application. A mask may be, but is not necessarily, dynamically reconfigured during testing in the manner described in the NETRA patent application.

Figure 12A:
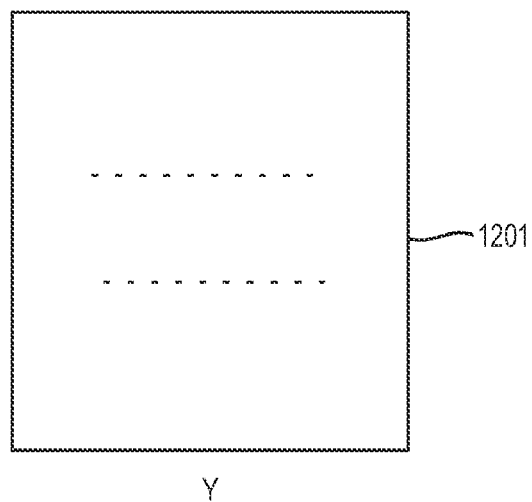
FIG. 12A is a diagram of a mask with two dashed lines.
Figure 12B:
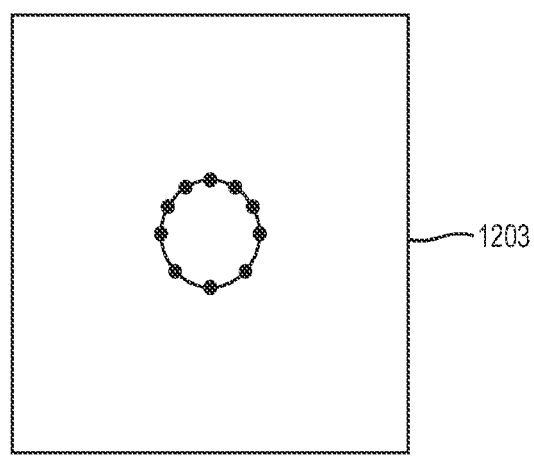
FIG. 12B is a diagram of a mask with a circular pattern of pinholes

FIGS. 12A and 12B show two masks that avoid cross talk and increase the resolution of the measuring channel.

FIG. 12A shows a mask 1201 which has two sequences of pinholes forming two dashed lines that have an offset by one pinhole from one line to the other. It allows the creation of Vernier tasks and super-resolution. Each point on screen turns into a dashed line on the retina. When aligned the dashed lines turn into a single solid line. Since lines have an off-set from each other, the subject has a clear sense of how good is the alignment. Small errors in alignment are easily noticed.

FIG. 12B shows a mask 1203 which can increase accuracy of a computation of the angle of astigmatism (for use in a best fitting procedure to test for astigmatism, e.g., the best fitting procedure described in the NETRA patent application). Using this mask, the best fitting algorithm can run as follows: (i) test at 0-degree meridian; (ii) test at 90-degree meridian; (iii) if the test results have a difference in power less than a minimum amount of variation (e.g., 0.25 diopters), test at 45-degree; (iv) if the test results still have difference in power less than a minimum, the subject does not have astigmatism; (v) compute the best fitting procedure to estimate the axis of astigmatism and test at 45 degrees plus the current axis; (vi) test at 56 degrees plus the current axis; (vii) test at 34 degrees plus the current axis; (viii) test at the current axis of astigmatism. For every step, an additional measurement can be taken at the meridian 90 degrees away from the current testing meridian. Techniques that display a virtual 3D object may be applied to create the same (or a similar) effect.

A rotatable mask used in this algorithm can use color filters or polarization to reduce cross-talk among pinholes or between more or less transmissive portions of the mask. For example, light of a certain color passing through pinholes in a rotatable mask may be used for measurement purposes while light of a different color passing through another, translucent portion of the mask may be used as relaxation stimuli.

Figure 13:
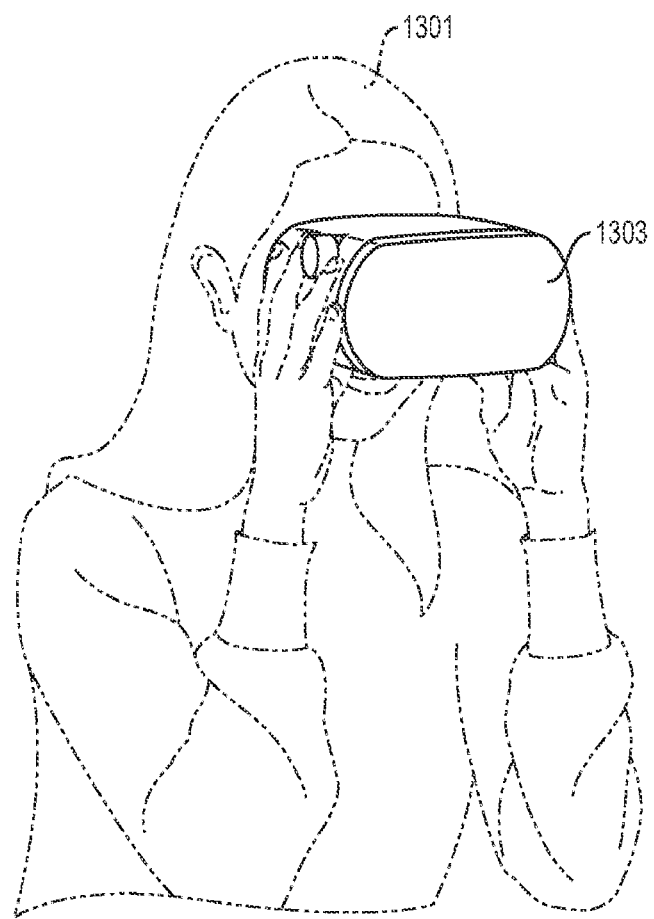
FIG. 13 shows a human subject holding a bi-ocular device.

Monocular and Bi-Ocular:

All of the embodiments of this invention described above and below can be implemented either monocularly or bi-ocularly. A bi-ocular implementation has a clear advantage of controlling convergence. In the example shown in FIG. 1, the bi-ocular apparatus induces the subject to look straight. Since convergence affects accommodation and pupil size, when looking straight, the subject tends to relax his eye and increase the pupil size. As both eyes are connected to the autonomous nervous system, the testing eye accommodation follows the stimulated idle eye. The result is a more accurate eye relaxation and a more stable measurement. The bi-ocular setup, in comparison to monocular designs, also: (i) reduces shuddering by requiring the viewer to hold the device with both hands allowing him to use a table to rest the elbows and (ii) reduces wrong device orientation due to the fact that the external surface of a bi-ocular device may conform to the general shape of the face around the eyes, thereby tending to prevent left and right tilting relative to the subject's face. The subject tends to hold a bi-ocular apparatus horizontally level up against the face, thereby reducing measurement errors. FIG. 13 shows an example of a user 1301 holding a bi-ocular device 1303 up to the face, with elbows resting on a desk (not shown) for stability.

Flipping a Bi-Ocular Apparatus:

Preferably, an apparatus for testing refractive aberration can measure both eyes. In many bi-ocular implementations of this invention, there are two distinct test and relaxation optical channels. In that case, there are at least two ways to test both eyes: (i) the testing and relaxation optics can be duplicated for each eye with or without a switch to activate one of them at a time; or (ii) the apparatus can be configured to be flipped to test the other eye.

Figure 14B:
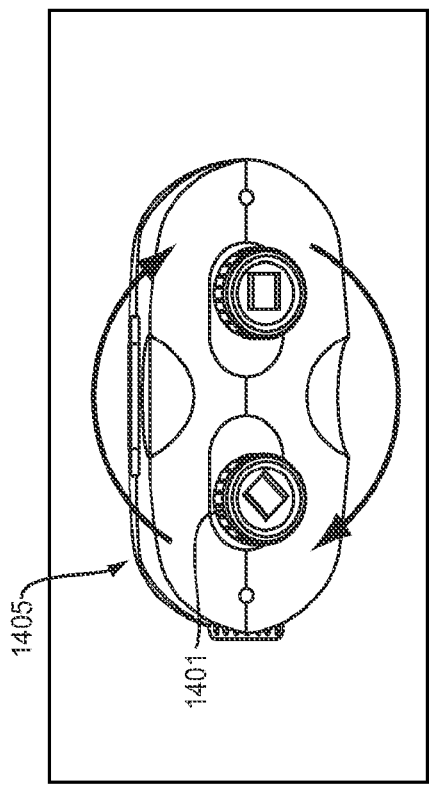
FIG. 14B is a diagram showing that the same bi-ocular apparatus in FIG. 14A can be "flipped" (rotated 180 degrees) to change which eye is being relaxed and which eye is being measured.
Figure 14A:
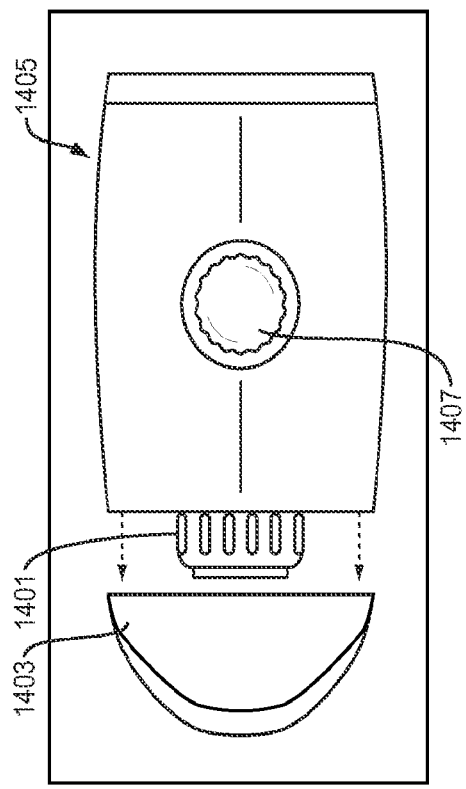
FIG. 14A is a side view of a bi-ocular apparatus with a removable cover.

FIGS. 14A and 14B illustrate flipping a bi-ocular device. FIG. 14A is a side view of the bi-ocular device 1405, including (i) a knob 1407 that a human can rotate to adjust the distance between optical channels for the right and left eyes, (ii) a dial 1401 around an optical channel, which a human can rotate to adjust a rotation angle of a mask for that channel, and (iii) a removable cover 1403 that provides a comfortable fit to the subject's face (e.g., with an indentation in the bottom center of the removable cover, which indentation conforms to the bridge of the nose). The removable cover 1403 also can shield the eyes from unwanted light rays (e.g., rays which come from the side, rather than through an optical channel). In FIG. 14A, the removable cover 1403 is being removed.

In FIG. 14B, the bi-ocular apparatus 1405 has been flipped (rotated 180 degrees), so that the eye channel formerly on the left side of the device is now on the right side of the channel. The removable cover 1403 can now be reattached to the apparatus 1405. In this example, the cover 1403 needed to be removed and reattached; otherwise the indentation for the nose bridge would be facing up—rather than down—after the apparatus 1405 is flipped.

Removing Cross-Talk

Cross-talk can occur when both relaxation and testing stimuli are presented to the same eye, and light that should go through an optical element that helps generate a relaxation image instead goes through an optical element that helps generate a testing image. Also, cross-talk can happen when the light that is generated for a given pinhole on a measurement mask goes through another pinhole. The methods described below account for both situations.

To mitigate or eliminate such cross-talk, any one or more of the following strategies may be employed: (i) color selectivity may be enforced (e.g., by one or more color filters or one or more color-specific light emitters) to cause light of a particular color to be used to generate stimuli for relaxing an eye, and to cause light of a different color to be used to generate stimuli for measuring refractive aberration of an eye; (ii) polarization state selectivity may be enforced (e.g., by one or more polarizers) to cause light of a particular polarization state to be used to generate stimuli for relaxing an eye, and to cause light of a different polarization state to be used to generate stimuli for measuring refractive aberration of an eye; and (iii) tubes or other occluders may serve as blocking walls.

In the case of (i), requisite color selectivity may be achieved by combining one or more color filters with one or more optical elements that are not color selective so that light which passes through the combination and emerges from the combination is color selective. In the case of (ii), requisite polarization state selectivity may be achieved by combining one or more polarizers with one or more optical elements that are not polarization state selective so that light which passes through the combination and emerges from the combination is polarization state selective. In the case of (iii), preferably, such tubes or other occluders are opaque and do not cause significant internal reflection. Light sources beyond the display may help to generate different polarization states.

As used herein, the term "polarizer" shall be construed broadly. For example, "polarizer" includes polarization filters and polarization state rotators.

Figure 15:
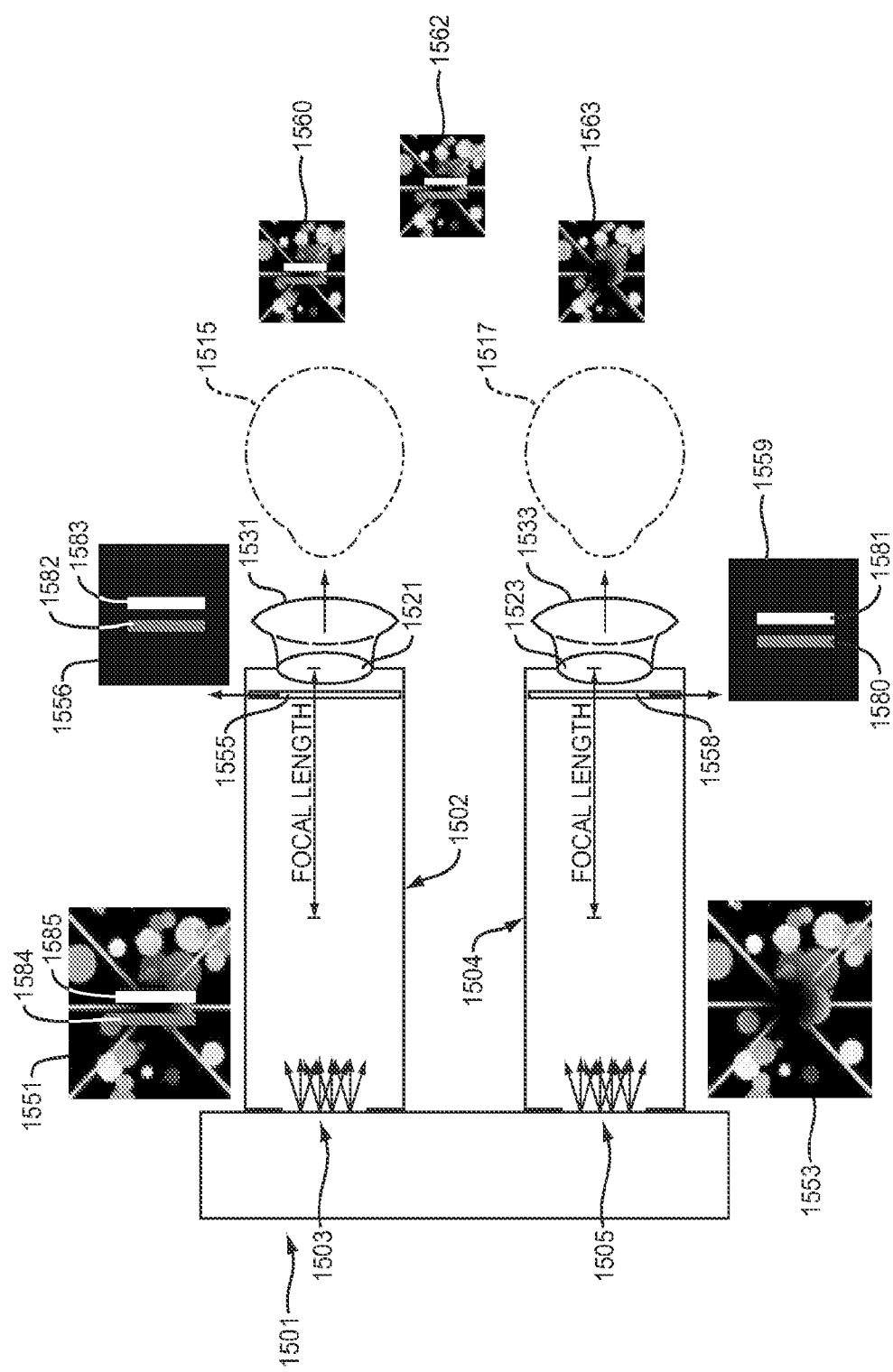
FIG. 15 is a cross-sectional schematic of a bi-ocular apparatus with color filters for avoiding cross-talk between relaxation and test cues.

FIG. 15 illustrates an example of an apparatus that eliminates such cross-talk, using color selectivity. In this example, a handheld display device (e.g., a cell phone) 1501 displays images in two regions 1503, 1505 of a screen.

In FIG. 15, mask 1555 is shown in side view (actual position) at 1555 and in frontal view (for clarity of presentation) at 1556. Likewise, mask 1558 is shown in side view (actual position) at 1558 and in frontal view (for clarity of presentation) at 1559.

In the example shown in FIG. 15, light travels through optical channel 1502 to the right eye 1515 as follows: Screen region 1503 displays image 1551. Part of image 1551 is blue—it consists primarily of different shades or tints of blue. Image 1551 also includes a red line 1584 and a green line 1585. Mask 1555 has three color filters: (1) filter 1582, which allows primarily red light to pass, (2) filter 1583, which allows primarily green light to pass, and (3) the remainder of mask 1556, which is a filter that allows primarily blue light to pass. Under these circumstances, primarily red light from red line 1584 can pass through filter 1582; primarily green light from green line 1585 can pass through filter 1583; and primarily blue light from the remainder of image 1551 can pass through the remainder of mask 1556.

Likewise, light travels through optical channel 1504 to the left eye 1517 as follows: Screen region 1505 displays image 1553. Image 1553 is blue—it consists primarily of different shades or tints of blue. Image 1553 does not include a red line or a green line. Mask 1558, which is seen in side view in 1558 and in frontal view in 1559, has three color filters: (1) filter 1580, which allows primarily red light to pass, (2) filter 1581, which allows primarily green light to pass, and (3) the remainder of mask 1559, which is a filter that allows primarily blue light to pass. Under these circumstances (where there are no red or green pixels in image 1553), primarily blue light passes through mask 1558.

In this example, image 1563 (which is blue) is presented to the left eye, and image 1560 (which is blue, red and green) is presented to the right eye. When both of the subject's eyes are open, the subject perceives image 1562.

In this example, the blue light is a relaxation stimulus which is presented to both the right and left eyes, and the red and green lines are testing stimuli that are presented to only the right eye.

In this example, the subject sees the blue image in both eyes. The blue image can be placed into any virtual position (i.e., its apparent position changed) by optical elements (e.g., by a lens) The apparent position of the blue image determines the eye convergence required for the subject to see the pattern well. Controlling eye convergence helps to control eye relaxation.

The width or narrowness of the bandpasses (e.g. color filters or polarizers) determines how selective these are. If color filters act as sufficiently narrow bandpasses, then the word "primarily" in the above description of FIG. 15 can be replaced by "only" (e.g. rather than let through primarily blue light, a filter may let through only blue light).

The apparatus in FIG. 15 could, instead, have been implemented using polarizers (instead of color filters) and polarization state selectivity (instead of color selectivity), monocularly or binocularly.

In some implementations of this invention: an apparatus for refractive aberration testing/relaxation of accommodation can: (A) use color filters in a mask in such a way that the wavelengths being cast match only one pinhole or feature on the mask; (B) use a different level of polarization for each feature or pinhole in the mask, in such a way that the polarized light from the screen passes mostly through one feature; and (C) create tubes that connect the mask and the screen and serve as blocking walls; For (B), the polarization state of the light on the screen may be changed by adding polarizers or polarization rotors. For (C) the tubes can be opaque and avoid internal reflection.

Rotation of Masks:

A mask with two openings can be rotated to test different meridians instead of requiring a mask with pinholes in a circle. The current rotation of the mask can be captured in a photo taken by the display device (e.g., cell phone) and the display device may display test patterns on positions that match the rotated mask. In a different implementation, the phone can rotate with the mask. The software then can use the accelerometers and other sensors to compute the measuring meridian. In case of rotating the phone, the software can use color channels to triple the current resolution. Since the phone is being rotated, all the measurements are being executed horizontally on screen space. Thus color channels can be used to increase accuracy for astigmatism.

Figure 16:
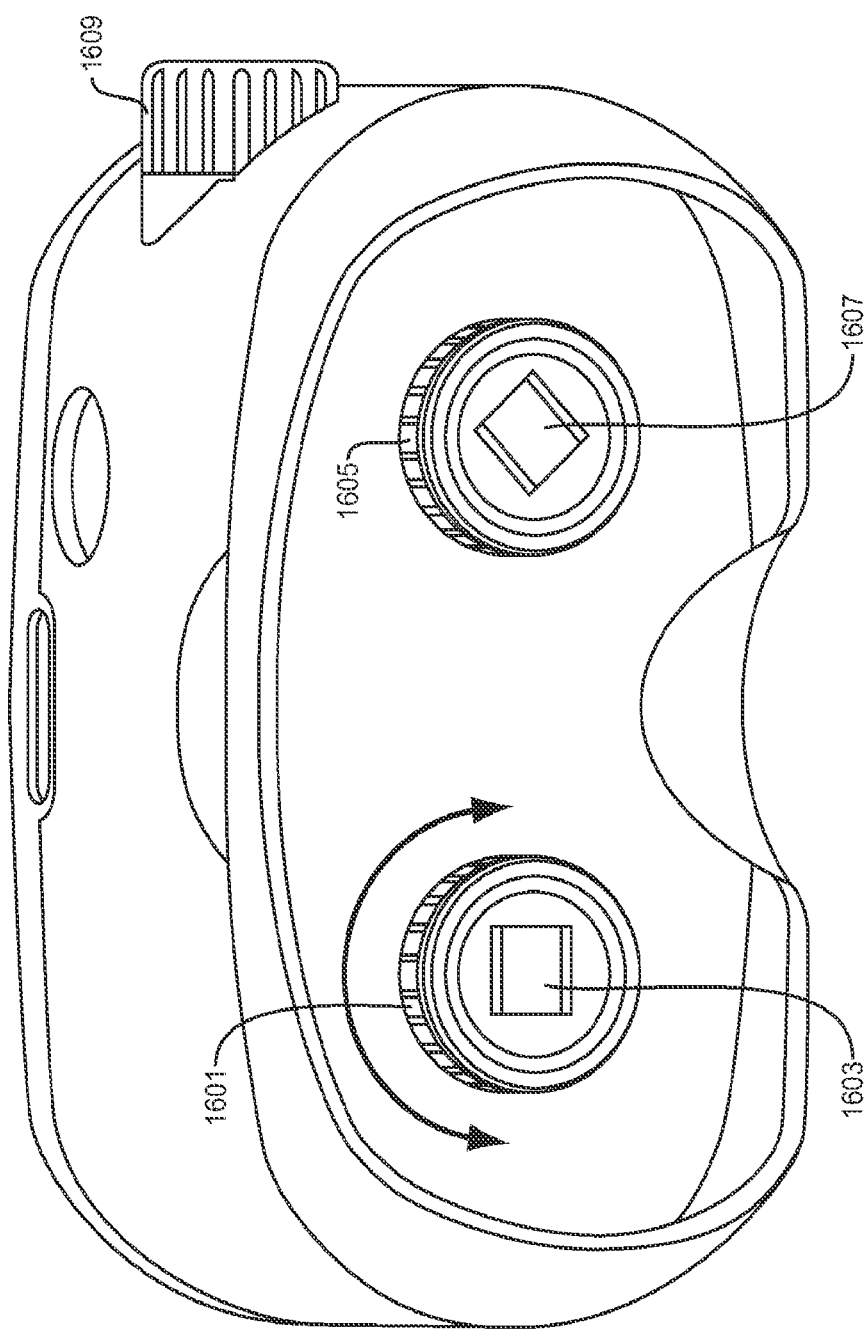
FIG. 16 is a diagram showing a knob which can be turned by a human to change rotational angle of a mask.

In the example shown in FIG. 16, rotatable grips 1601, 1605 on the exterior of two optical channels can be used to rotate masks 1603, 1605, respectively. A rotatable dial 1609 can be rotated by a human in order to adjust the distance between the two optical channels.

Mitigating Prismatic Effects

In exemplary implementations of this invention, prismatic effects are an undesirable artifact that can be mitigated. Prismatic effects can shift the perception of the relaxation image, making the subject converge his eyes to a given depth and thus accommodate (rather than relax) his eyes. The prismatic effects can be created by a misalignment between the optical axes of lens in the subject's eyes and the optical axes of lenses (if any) in the apparatus. Changing the distance between the optical axes of lens of the apparatus, in order to align them with the optical axes of lens in the subject's eye, can correct for prismatic effects. In this case, all the optical components and images in the image should be shifted, including the image displayed on the display screen (e.g., displayed on screen regions 103, 503, 703, 1003).

Figure 17:
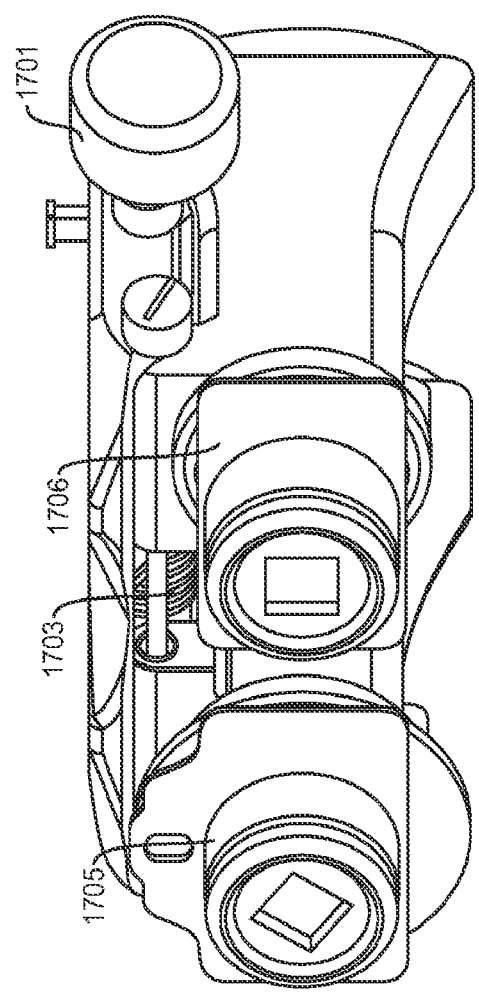
FIG. 17 is a diagram showing a knob on a bi-ocular apparatus, which knob can be turned by a human to control the distance between the right and left optical channels of the apparatus.
Figure 18:
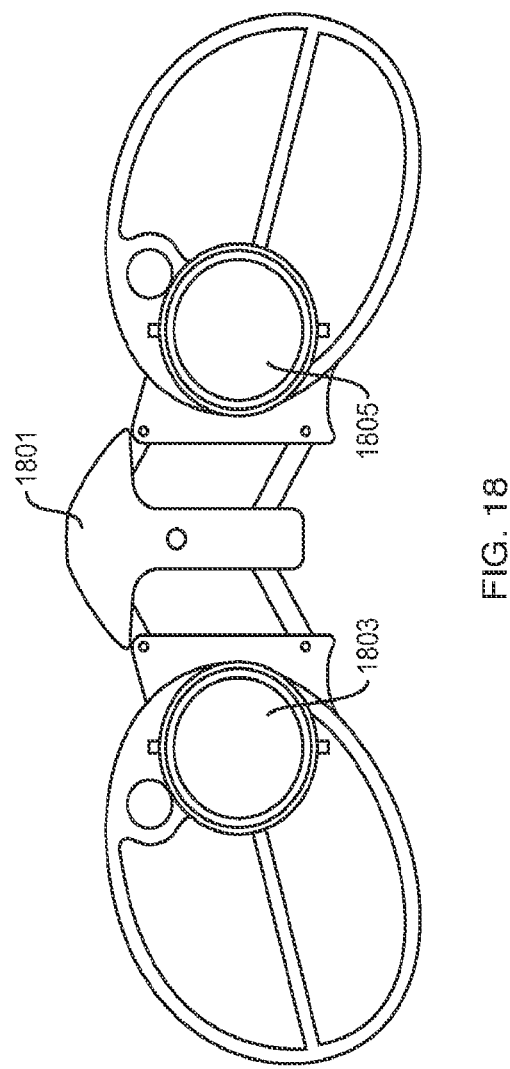
FIG. 18 is a diagram showing a hinged joint on a bi-ocular apparatus, which hinged joint can be moved by a human to control the distance between the right and left optical channels of the apparatus.

FIGS. 17 and 18 show two different mechanisms that can be used to adjust the distance between optical channels in a bi-ocular apparatus, so that it matches the user's pupillary distance, in order to mitigate prismatic effects.

In FIG. 17, two optical "trumpets" 1705, 1706 include lenses, masks and films for presenting test stimuli to the test eye through one channel and relaxation stimuli to the idle eye, one "trumpet" for each channel. A user is able to move the two channels closer together or further apart by rotating a knob 1701. The knob is rigidly coupled to a shaft on which two oppositely threaded worm gears 1703 are also rigidly attached. By rotating the knob, the worm gears are also rotated. The worm gears are each in contact with an optical channel by means of a rack gear. The nature of the interaction between a worm gear and a rack gear is such that when the worm gear rotates, the rack gear (and everything attached to it) is moved in a linear manner in one direction. Thus when the knob is rotated, the lens assemblies are moved linearly by the rotation of the worm gears. Because the two worm gears are oppositely threaded (one left hand threaded and one right hand threaded), the two lens assemblies move in opposite directions for a given rotation of the knob.

In the example shown in FIG. 18, a user can move two optical channels (e.g., 1803, 1805) together or further apart by pushing or pulling on a central beam 1801 while holding housings for the optical channels like a pair of binoculars. The central beam is attached to each optical channel by two linkages, creating a four bar linkage system. This linkage system allows the optical channels to maintain their rotational orientation with respect to a subject's eyes while moving closer together or further apart in order to match the subject's pupillary distance.

Alternatively, the position of a relaxation image can be translated, perpendicular to the optical axis of the relaxation optical channel, in order to correct for prismatic effect. For example, if the relaxation image is displayed on a film 107, the film can be translated perpendicular to the optical axis of the relaxation channel 104. Or, for example, if the relaxation image is displayed directly on a screen, and a film is not interposed between the screen and eye, then the position at which the image is displayed may be shifted on the screen. Prentice's Rule is an approximation to estimate prismatic effect and states that the decentration of a lens in centimeters times the power of the lens is equal to the prismatic effect. The formula for Prentice's Rule is: $\Delta = c \ast F$. After the prismatic effect is measured, it can be compensated for by moving the film or the image on screen (as the case may be) against the convergence factor $\Delta$ created by the effect.

Sub-Pixel Displacements:

In some implementations of this invention, sub-pixel displacements are used to create super-resolution. For example, a sinusoidal pattern can be created with ten times more pixels than the resolution on screen in the testing optical channel. Every ten pixels squared of the pattern may form a single pixel on screen. The ten pixels squared can be averaged or a representative pixel out of them can be displayed on screen. The test patterns on screen may move by 0.1 screen pixels (instead of moving by 1 screen pixel). Because the pixel value being averaged or picked changes for every tenth of a displacement, the subject notices a difference in the appearance of the pattern.

For example, sub-pixel displacements can be employed, in the testing optical channel, to facilitate vernier acuity applications. For example, the test pattern displayed in the testing optical channel may be a sinusoidal curve in which the sine is drawn perpendicular to the current meridian. The sine pattern can be duplicated in the meridian angle in such a way that it creates a variation of a dashed line. Two lines are displayed on screen, one behind each used feature of the mask. One line can have an offset equal to the width of the sine dash, in such a way that the subject sees a solid sinusoidal line when both lines from the screen are aligned. The same dashed pattern procedure can also be used for many other patterns.

Lens in Front of Mask:

In alternated implementations of all designs discussed above or below, the testing procedure can be done with an additional lens on top of the pinhole mask (e.g., lens 141 in FIG. 4). This setup is similar to FIG. 1, but the shift c (as defined herein) to compute the refractive error is measured from the center of the mask instead of from point on screen behind the respective mask's pinhole. In this case, there is no difference between the results for measuring myopia (usually represented by a minus sign) and hyperopia (usually represented by a plus sign). In alternative versions of this design, the mask can also be built inside the lens. The testing procedure may be the same as in FIG. 1.

Calibration

In some implementations, in order to calibrate a relaxation/testing apparatus, a camera focusing at infinity (rather than an eye focusing at infinity) can be measured. In this case, preferably: (a) the refractive correction for the camera is minimized to zero; (b) additional lenses with known powers are inserted in front of the camera and the measurement taken; (c) the absolute value of the resulting power matches the absolute power of the lens, and (d) by using a standard relay lens system, the camera of the phone can be optically translated to the position of the eye, looking inside the device. In this case, an electronics component that is projecting a stimulus can also assess stimulus quality and precision and be used to calibrate its own procedures.

Control, Actuation and Processing:

In some implementations of this invention, movements of one or more moveable parts are actuated by electronically-controlled actuators, and sensors measure data indicative of position or orientation of the parts.

Figure 19:
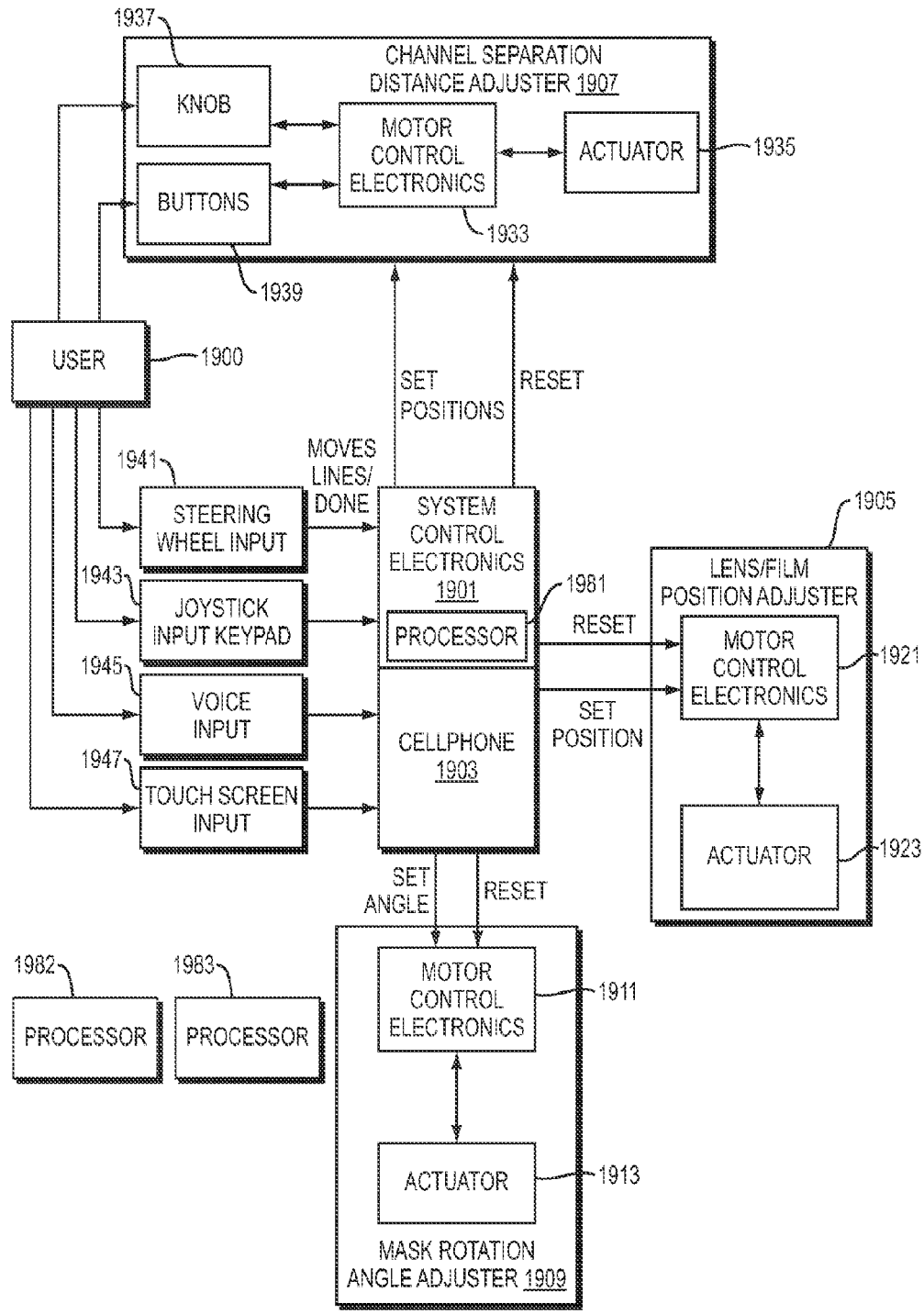
FIG. 19 is a block diagram of hardware for electronically-controlled actuation of certain moveable parts.

FIG. 19 is a block diagram of hardware for electronically-controlled actuation of certain moveable parts. System control electronics 1901 may be housed in or adjacent to a cellphone 1903. The electronics control a lens/film position adjuster 1905, a channel separation distance adjuster 1907, and a mask rotation angle adjuster 1909. The lens/film position adjuster 1905 (a) controls the distance between a lens and a film; and (b) comprises motor control electronics 1921 and actuator 1923. The mask rotation angle adjuster 1909 (a) controls angle of rotation of a mask; and (b) comprises motor control electronics 1911 and actuator 1913. The channel separation distance adjuster 1907 controls the distance between optical axes of the optical channels of the apparatus (in order to make that distance equal to the subject's pupillary distance). The channel separation distance adjuster 1907 comprises motor control electronics 1933 and actuator 1935. It also includes a knob 1937, buttons 1939 or other input mechanisms for accepting input from a human. Input devices accept at least the following input from a human 1900: steering wheel input 1941, joystick input keypad 1943, voice input 1945, and touch screen input 1947.

Figure 20:
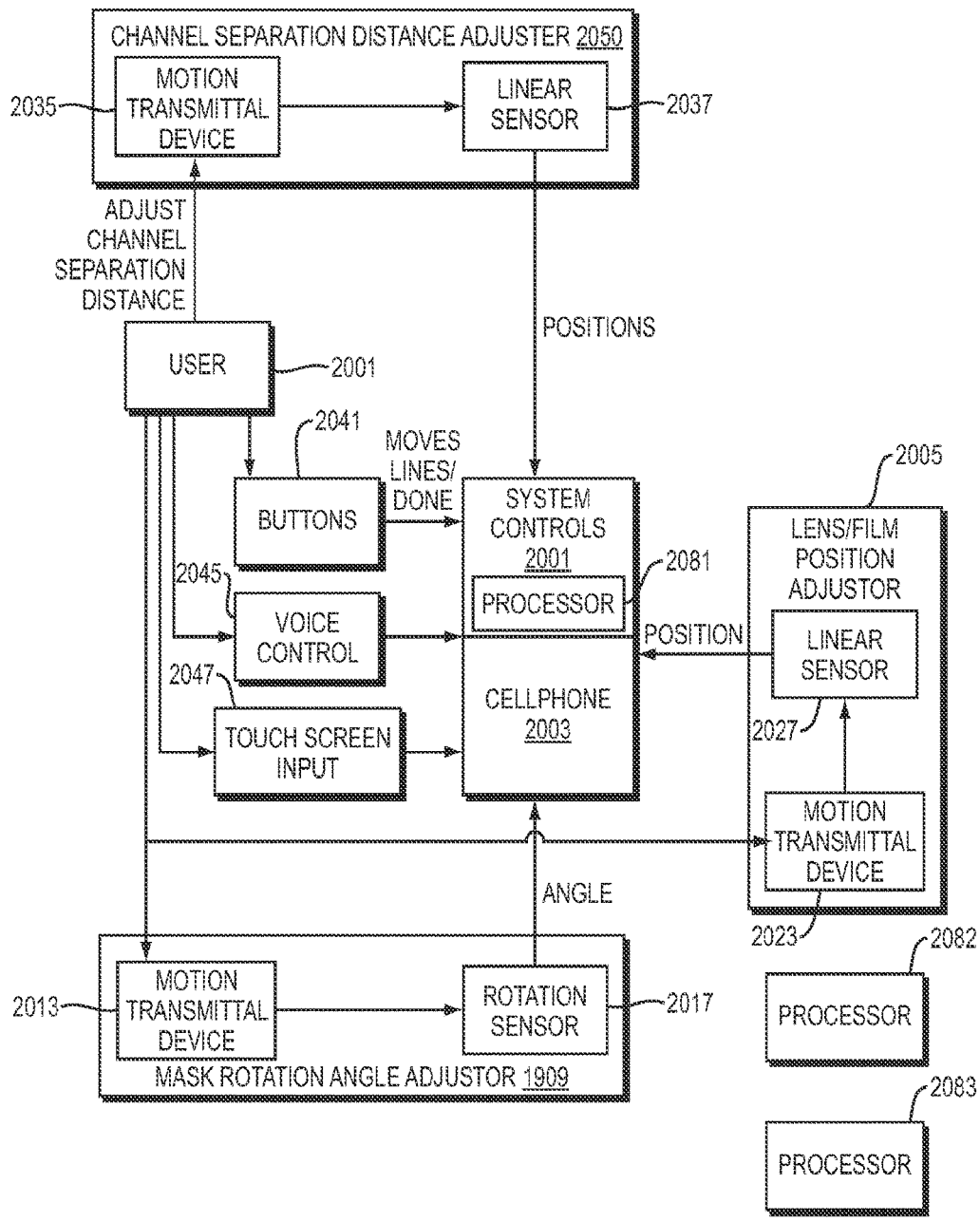
FIG. 20 is a block diagram of hardware components of a system, in which motion of certain components is powered by movements of a human.

In some implementations of this invention, movements of one or more moveable parts are powered by motion of a human, and sensors measure data indicative of position or orientation of the parts. An example of this is shown in FIG. 20. Motion of a human user 2001 may be transformed or transmitted, via a motion transmittal device (e.g., 2013, 2023, 2035) into linear or rotational movement of a moveable part of the apparatus. For example, in a lens/film position adjuster 2005, human motion can be transmitted or transformed into linear movement of a lens or film in order to adjust lens/film distance, and a linear sensor 2027 may take reading indicative of position of the lens or film. Or, for example, in a mask rotation angle adjuster 1909, human motion can be transmitted or transformed into rotation of a mask, and a rotation sensor 2017 may take readings indicative of angle of the mask. Or, for example, in a channel separation distance adjuster 2050, human motion can be transmitted or transformed into linear movement of a two optical channels relative to each other, and a linear sensor 2037 may take readings indicative of that distance. System controls 2001 housed in or adjacent to a display device (e.g., cell phone) 2003 may receive and process data, including data indicative of input from a human or of sensor measurements. For example, the input from a human may delivered via buttons 2041, voice control 2045 or touch screen 2047. For example, the sensor measurements may be received from sensors 2017, 2027, 2037.

In exemplary implementations of this invention, mechanisms are used to translate or rotate movable parts. One or more of these mechanisms can be automated and electronically controlled, including by the same device controlling the display, such as a smartphone. Communication between integrated electronics and the smartphone can be over any protocol, such as Bluetooth protocol, wireless networks, USB serial protocol and via the audio jack. Electronics (e.g., for processing and control) can even be powered by a USB connector or by audio waves.

In exemplary implementations of this invention, one or more computer processors are specially adapted: (1) to control the operation of hardware components of an apparatus for relaxing an eye and testing refractive aberration (which hardware may include one or more electronic displays, actuators, light sources, cameras, and visual displays); (2) to perform processing of sensor measurements and input from humans (3) to receive signals indicative of human input, (4) to output signals for controlling transducers for outputting information in human perceivable format, and (5) to process data, perform computations, and control the read/write of data to and from memory devices. The one or more processors may be located in any position or position within or outside of the relaxation/testing device. For example: (1) at least some of the one or more processors may be embedded within or housed together with other components of the device, such as an adaptive lens, and (2) at least some of the one or more processors may be remote from other components of the device. The one or more processors may be connected to each other or to other components in the testing/relaxation optical apparatus either: (1) wirelessly, (2) by wired connection, or (3) by a combination of wired and wireless connections. For example, rectangles 1981, 1982, 1983, 2081, 2082, 2083 (in FIGS. 19 and 20) each, respectively, represent one or more of these computer processors.

Definitions and Clarifications:

Here are a few definitions and clarifications. As used herein:

The terms "a" and "an", when modifying a noun, do not imply that only one of the noun exists.

The term "actuator" shall be construed broadly. For example, an "actuator" may include a motor and a motion transmittal mechanism that transforms or transmits movement of a part of the motor. The term "actuator" also includes a motion transmittal mechanism (e.g., a gear) powered by external source (e.g., a human). An "actuator" never includes a living organism.

The term "adaptive lens" shall be construed broadly. For example, an "adaptive lens" may comprise: (i) a liquid lens (the power of which can be changed by changing the amount of liquid inside); (ii) an electrowetting lenses (the lens curvature of which can be changed by changing liquid surface tension); (iii) an electroactive lens (in which the refractive index of liquid crystals inside the lens can change); (iv) Alvarez lenses (which can slide on top of each other to change optical power); or (v) an adaptive optics device (e.g., comprising an array of deformable mirrors or MEMs).

The term "depth dependent anistropic image formation" (or "DAF") means the process of computing a light field to display a virtual object at different points in space. For example, the following method comprises DAF: computing a light field that displays one or more virtual 3D objects at given distances from the eye. Also, for example, the following method comprises DAF: given as input an expected image to be received by the retina of the subject's eye, calculate the light field to be shown on a specified display. Also, for example, the following method comprises DAF: (i) pairing individual light-field rays (e.g., rays generated from a double stack of LCDs) and retinal positions to associate a raw intensity to each ray; and (ii) normalizing retinal "pixels". For example, DAF can be used to compute: (a) the projection of depth-dependent anisotropic patterns that account for spatially-distributed optical aberrations of an eye that is being measured; and (b) depth-dependent patterns virtually placed at the right point in focus for a given optical power.

An "DAF image" is an image of a virtual object calculated by depth dependent anistropic image formation. In practice, a "DAF image" is computed from an incomplete sample of all possible light rays in a light field. A display of an "anistropic image" may vary temporally. A DAF image may be pre-computed or computed in real time, in each case relative to the time it is displayed.

The term "comprise" (and grammatical variations thereof) shall be construed broadly, as if followed by "without limitation". If A comprises B, then A includes B and may include other things.

A "dash mask" means a mask which, when illuminated, displays a pattern that includes dashed lines. For example, this pattern may include two dashed straight lines. (FIG. 12A shows an example of this). However, a dash mask is not limited to straight lines or to a particular number of dashed objects.

The terms "e.g.", "such as" and "for instance" mean for example.

The fact that an "example" or multiple examples of something are given does not imply that they are the only instances of that thing. An example (or a group of examples) is merely a non-exhaustive and non-limiting illustration. If any examples of a thing are listed, many other examples of the thing may exist.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each can be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes "a third" thing, a "fourth" thing and so on shall be construed in like manner.

In the context of an optical device (and components of the device), "front" is optically closer to a viewer, and "rear" is optically further from the viewer, when the viewer is viewing the device during normal operation of the device. The "front" and "rear" of a device continue to be the front and rear, even when no viewer is present.

Two sets "fully overlap" if and only if they are identical. For example, a first set of colors and a second set of colors do not fully overlap if they include the same frequencies but the intensity distribution of the frequencies differs from the first set to the second set (e.g., if red is much more intense in the first set than in the second). Or, for example, a first set of polarization states and a second set of polarization states do not fully overlap if they include the same polarization states but the intensity distribution of the polarization states differs from the first set to the second set (e.g., if light of a particular polarization state is much more intense in the first set than in the second).

Headings herein (such as "Lens and Film" or "Definitions and Clarifications") are for convenience only, and do not affect the meaning, construction, or interpretation of any document.

The terms "horizontal" and "vertical" shall be construed broadly. For example, "horizontal" and "vertical" may refer to two arbitrarily chosen coordinate axes in a Euclidian two dimensional space.

The term "include" (and grammatical variations thereof) shall be construed broadly, as if followed by "without limitation".

A "first light source" and "a second light source" may, for example, be: (a) separate light sources (e.g., separate display screens) or (b) different regions of a single display screen.

The term "line" shall be construed broadly. For example, the term "line" includes a straight line, a curved line or a dashed line.

The term "mask" includes a static mask and a temporally varying mask.

The term "or" is inclusive, not exclusive. For example "A or B" is true if A is true, or B is true, or both A or B are true. Also, for example, a calculation of "A or B" means a calculation of A, or a calculation of B, or a calculation of A and B.

A parenthesis is simply to make text easier to read, by indicating a grouping of words. A parenthesis does not mean that the parenthetical material is optional or can be ignored.

A "pinhole mask" may have one or more pinholes. For example, a "pinhole mask" may have (i) only one pinhole or (ii) multiple pinholes.

A "pinhole pair mask" means a mask which, when illuminated, displays a pattern that: (i) rotates over time, (ii) has a center of rotation, and (iii) includes one or more pairs of pinholes, the pinholes in each respective pair being equidistant from the center of rotation and being in a straight line that intersects the center of rotation. The distance between pinholes and the center of rotation may, but does not necessarily, vary from pair to pair. The pinholes in a pinhole pair mask may be arranged in a circle (FIG. 12B shows an example of this). However, a pinhole pair mask is not limited to circular patterns.

The "power" of an optical device (e.g., a lens, lenslet array or multi-lens optical system) means the optical power of the optical device.

The term "progressive lens" shall be construed broadly. For example, the term "progressive lens" means any lens whose power spatially varies over a core region (as defined below) of the lens by at least 20% in a continuous gradient or in discrete steps. Furthermore, the term "progressive lens" includes an array of lenslets, which when taken as whole have a power which spatially varies, over the array taken as a whole, by at least 20% in a continuous gradient or in discrete steps. For purposes of this definition of "progressive lens", a "core region" of a progressive lens consists of a set of points, wherein each respective point in the set (i) is within the lens, (ii) is in an intersection plane (as defined below) of the lens, and (iii) is positioned such that the shortest distance to an edge of the lens from the respective point along any straight line that lies in the intersection plane is equal to at least 10% of the distance between edges of the lens measured along that line. For purposes of this definition of progressive lens, an "intersection plane" of a progressive lens is a plane that is (i) perpendicular to the optical axis of the lens and (ii) has an area of intersection with the lens that is greater than or equal to the largest area of intersection with the lens, out of all planes that are perpendicular to the optical axis.

The term "set" does not include the null set. A set must always have at least one element.

The term "shift c" means the term "c" in the following equation: c=(f/a)/(d−t), where t is the distance from a pinhole array to an eye, a is the spacing between the pinholes in the pinhole array, d is the apparent distance of a virtual scene point from the eye; and f is the distance between the pinhole array and a display screen illuminating the pinhole array, which display screen is optically further from the eye than the pinhole array.

The term "subject" means a human whose eye is being tested for refractive aberration by, or whose eye is being relaxed by, an apparatus. For example, a "subject" may be a person who is using an apparatus to self-administer the test or to self-administer the eye relaxation. Or, for example, a "subject" may be a patient, and another person may be using the apparatus to administer the test to the patient or to relax the eye of the patient.

Notwithstanding anything to the contrary herein, the term "tangible machine-readable media" does not include any transitory, propagating signal. For example, "tangible machine-readable media" does not include (a) any electromagnetic wave or impulse; and (b) any mechanical wave or impulse.

The terms "refractive aberration", "test for refractive aberration", "measure refractive aberration", and terms of like import shall be construed broadly. For example, a test for refractive aberration includes any measurement of, or attempt to detect, an optical aberration of the eye, including myopia, hyperopia, astigmatism, spherical aberration, coma, trefoil, halos, glare, or any other higher order or lower optical aberrations. Also, for example, a test for refractive aberration includes any measurement of optical power or refraction characteristics of the crystalline lens or optical system of a human eye.

Variations:

This invention may be implemented in many different ways. Here are some non-limiting examples.

In the examples above where light passes through two masks on the way to an eye, one of the masks can be replaced with a lenslet array. For example, in FIG. 21, item 2110 may be a lenslet array rather than a mask. In that case: (a) light that passes through both the mask and the lenslet array may be used to form an image of a virtual object; and (b) apparent depth of the virtual object may vary temporally.

All optical channels may be protected from exterior light such that the subject only receives light from the display.

Cycloplegic and other eye relaxing drops may be used to ensure the eye's relaxation.

In each of the embodiments discussed herein, the apparatus can induce an eye to focus over a range of depths, including by tensing or relaxing the ciliary muscle. Different depths of focus require different levels of relaxation/tension of the ciliary muscle. Tension is the inverse of relaxation, so every change in relaxation is a change in tension. Saying that an apparatus can induce relaxation of the eye is a succinct way of saying that the apparatus can induce changes in accommodation/tension/relaxation of the eye (including its ciliary muscle), including causing the ciliary muscles to tense or relax, and can thereby change the depth at which the eye focuses.

In all embodiments in which a screen region (e.g., 105) backlights a film (e.g., 107), the screen region may display a pattern. The pattern can, for example, be a simple white steady square or a dynamic image. The brightness of the pattern displayed by the screen region (e.g., 105) can adjust the brightness of the backlit film (e.g., 107). The colors of the pattern displayed by the screen region (e.g., 105) may change the perceived color of the film the screen region (e.g., 107). For example, given that many people focus on wavelengths around the green color, the film may be illuminated with only green pixels to facilitate accommodation control. The screen region (e.g., 105) can display many patterns according to the design and film.

This invention is not limited to display screens in cellphones or other handheld electronic devices. For example, this invention may be used with any electronic display screen or any other appropriate light source.

This invention may be implemented as a method of presenting stimuli during a time period to a human who has a first eye and a second eye, which method comprises using optical apparatus to display a first set of visual stimuli to the first eye to change accommodation of the first eye, while: (a) using the apparatus to display a second set of visual stimuli to the first or second eye to measure refractive aberration of the first or second eye; and (b) using one or more polarizers or color filters to cause (i) the first set of stimuli to be only light of a first set of colors and the second set of stimuli to be only light of a second set of colors, wherein the first and second set of colors do not fully overlap, or (ii) the first set of stimuli to be only light of a first set of polarization states and the second set of stimuli to be only light of a second set of polarization states, wherein the first and second set of polarization states do not fully overlap. Furthermore: (1) light in the second set of visual stimuli may pass through a mask before reaching the human; (2) the mask may comprise a light attenuation pattern that varies both spatially and temporally during the time period; (3) the mask may comprise a dash mask; (4) the second set of visual stimuli may apparently comprise two dashed two lines that are apparently separate at a first time during the time period and that apparently align into a single solid line at a second time during the time period; (5) temporal variation of the pattern during the time period may include rotation of the pattern; (6) the mask may comprise a pinhole pair mask; (7) the apparatus may be bi-ocular, and the first set of visual stimuli may be presented to the first eye but not the second eye while the second set of visual stimuli is presented to the second eye but not the first eye; (7) the apparatus may be bi-ocular, and the first set of visual stimuli may be presented to both the first and second eyes while the second set of visual stimuli is presented to the second eye but not the first eye; and (8) the apparatus may be monocular, and both the first and second sets of visual stimuli may be presented to the first eye at the same time.

This invention may be implemented as apparatus for presenting stimuli during a time period to a human who has a first eye and a second eye, the apparatus comprising in combination: (a) a first light source; (b) a second light source; (c) a plurality of optical elements, including one or more polarizers or color filters; and (d) a plurality of optical elements; wherein (i) the plurality of optical elements are configured to modify light from the first light source to display a first set of visual stimuli to the first eye to change accommodation of the first eye, while modifying light from the second light source to display a second set of visual stimuli to the first or second eye to measure refractive aberration of the first or second eye, and (ii) the one or more polarizers or color filters are configured to cause (A) the first set of stimuli to be only light of a first set of colors and the second set of stimuli to be only light of a second set of colors, wherein the first and second set of colors do not fully overlap; or (B) the first set of stimuli to be only light of a first set of polarization states and the second set of stimuli to be only light of a second set of polarization states, wherein the first and second set of polarization states do not fully overlap. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements, such that: (a) the plurality of optical elements display a first set of visual stimuli to the first eye of a human to change accommodation of the first eye, while displaying a second set of visual stimuli to the first eye or a second eye of the human to measure refractive aberration of the first or second eye, and (b) one or more polarizers or color filters cause (i) the first set of stimuli to be only light of a first set of colors and the second set of stimuli to be only light of a second set of colors, wherein the first and second set of colors do not fully overlap; or (i) the first set of stimuli to be only light of a first set of polarization states and the second set of stimuli to be only light of a second set of polarization states, wherein the first and second set of polarization states do not fully overlap; wherein the plurality of optical elements includes the one or more polarizers and color filters.

This invention may be implemented as a method of presenting stimuli to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein: (a) the second set of visual stimuli (i) includes light that passes through a first region of a mask to reach a first region of a pupil of the human and (ii) includes light that passes through a second region of the mask to reach a second region of the pupil, which first and second regions of the mask do not overlap each other and which first and second regions of pupil do not overlap each other; and (b) the method further comprises using one or more color filters or polarizers to cause (i) the light that passes through the first region to be only light of a first set of colors and the light that passes through the second region to be only light of a second set of colors, wherein the first and second set of colors do not fully overlap; or (ii) the light that passes through the first region to be only light of a first set of polarization states and the light that passes through the second region to be only light of a second set of polarization states, wherein the first and second set of polarization states do not fully overlap. Furthermore: (1) light in the second set of visual stimuli may pass through a mask before reaching the human; (2) the mask may comprise a light attenuation pattern that varies both spatially and temporally during the time period; (3) the mask may comprise a dash mask; (4) the second set of visual stimuli may apparently comprise two dashed two lines that are apparently separate at a first time during the time period and that apparently align into a single solid line at a second time during the time period; (5) temporal variation of the pattern during the time period may include rotation of the pattern; (6) the mask may comprise a pinhole pair mask; (7) the apparatus may be bi-ocular, and the first set of visual stimuli may be presented to the first eye but not the second eye while the second set of visual stimuli is presented to the second eye but not the first eye; (7) the apparatus may be bi-ocular, and the first set of visual stimuli may be presented to both the first and second eyes while the second set of visual stimuli is presented to the second eye but not the first eye; and (8) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; and (c) a plurality of optical elements, including (i) a mask, and (ii) one or more polarizers or color filters; wherein (i) the plurality of optical elements are configured to modify light from the first light source to display a first set of visual stimuli to the first eye to change accommodation of the first eye, while modifying light from the second light source to display a second set of visual stimuli to the first or second eye to measure refractive aberration of the first or second eye, (ii) the mask is positioned such that the second set of visual stimuli (A) includes light that passes through a first region of a mask to reach a first region of a pupil of the human and (B) includes light that passes through a second region of the mask to reach a second region of the pupil, which first and second regions of the mask do not overlap each other and which first and second regions of pupil do not overlap each other, and (iii) the one or more color filters or polarizers are configured to cause (A) the light that passes through the first region to be only light of a first set of colors and the light that passes through the second region to be only light of a second set of colors, wherein the first and second set of colors do not fully overlap; or (B) the light that passes through the first region to be only light of a first set of polarization states and the light that passes through the second region to be only light of a second set of polarization states, wherein the first and second set of polarization states do not fully overlap. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements, such that: (a) the plurality of optical elements display a first set of visual stimuli to the first eye of a human to change accommodation of the first eye, while displaying a second set of visual stimuli to the first eye or a second eye of the human to measure refractive aberration of the first or second eye, and (b) the second set of visual stimuli (i) includes light that passes through a first region of a mask to reach a first region of a pupil of the human and (ii) includes light that passes through a second region of the mask to reach a second region of the pupil, which first and second regions of the mask do not overlap each other and which first and second regions of pupil do not overlap each other; and (c) one or more polarizers or color filters (which one or more polarizers or color filters are included in the plurality of optical elements) cause (i) the light that passes through the first region to be only light of a first set of colors and the light that passes through the second region to be only light of a second set of colors, wherein the first and second set of colors do not fully overlap; or (ii) the light that passes through the first region to be only light of a first set of polarization states and the light that passes through the second region to be only light of a second set of polarization states, wherein the first and second set of polarization states do not fully overlap.

This invention may be implemented as a method of presenting stimuli during a time period to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein (a) the first set of stimuli includes light that passes through a progressive lens, which lens has a first region, a second region and other regions; (b) the optical power of the first region differs from the optical power of the second region by at least 5%; (c) at a first time during the time period, the first set of stimuli includes light that passes through the first region but does not include light that passes through the second region; (d) at a second time during the time period, the first set of stimuli includes light that passes through the second region but does not include light that passes through the first region; and (e) the first and second times do not overlap each other. Furthermore: (1) light in the second set of visual stimuli may pass through a mask before reaching the human; (2) the mask may comprise a light attenuation pattern that varies both spatially and temporally during the time period; (3) the mask may comprise a dash mask; (4) the second set of visual stimuli may apparently comprise two dashed two lines that are apparently separate at a first time during the time period and that apparently align into a single solid line at a second time during the time period; (5) temporal variation of the pattern during the time period may include rotation of the pattern; (6) the mask may comprise a pinhole pair mask; (7) the apparatus may be bi-ocular, and the first set of visual stimuli may be presented to the first eye but not the second eye while the second set of visual stimuli is presented to the second eye but not the first eye; (7) the apparatus may be bi-ocular, and the first set of visual stimuli may be presented to both the first and second eyes while the second set of visual stimuli is presented to the second eye but not the first eye; and (8) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; and (c) a plurality of optical elements, including a progressive lens; wherein (i) the progressive lens includes a first region, a second region and other regions, (ii) the optical power of the first region differs from the optical power of the second region by at least 10%, and (iii) the plurality of optical elements are configured to, during a time period, modify light from the first light source to display a first set of visual stimuli to the first eye to change accommodation of the first eye, while modifying light from the second light source to display a second set of visual stimuli to the first or second eye to measure refractive aberration of the first or second eye, such that (A) at a first time during the time period, the first set of stimuli includes light that passes through the first region but does not include light that passes through the second region, (B) at a second time during the time period, the first set of stimuli includes light that passes through the second region but does not include light that passes through the first region, and (C) the first and second times do not overlap each other. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements, such that: (a) during a time period, the plurality of optical elements display a first set of visual stimuli to the first eye of a human to change accommodation of the first eye, while displaying a second set of visual stimuli to the first eye or a second eye of the human to measure refractive aberration of the first or second eye; (b) the first set of stimuli includes light that passes through a progressive lens, which lens has a first region, a second region and other regions; (c) the optical power of the first region differs from the optical power of the second region by at least 5%; (d) at a first time during the time period, the first set of stimuli includes light that passes through the first region but does not include light that passes through the second region; (e) at a second time during the time period, the first set of stimuli includes light that passes through the second region but does not include light that passes through the first region; and (f) the first and second times do not overlap each other.

This invention may be implemented as a method of presenting stimuli during a time period to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein: (a) the apparatus includes a first set of optical fibers, a second set of optical fibers and other sets of optical fibers; (b) the first set of optical fibers terminates at a first optical distance from the first eye, and the second set of optical fibers terminates at a second optical distance from the first eye, (c) at a first time during the time period, the first set of stimuli includes light that passes through the first set of optical fibers but does not include light that passes through the second set of optical fibers; (c) at a second time during the time period, the first set of stimuli includes light that passes through the second set of optical fibers but does not include light that passes through the first set of optical fibers; and (d) the first and second times do not overlap each other. Furthermore: (1) light in the second set of visual stimuli may pass through a mask before reaching the human; (2) the mask may comprise a light attenuation pattern that varies both spatially and temporally during the time period; (3) the mask may comprise a dash mask; (4) the second set of visual stimuli may apparently comprise two dashed two lines that are apparently separate at a first time during the time period and that apparently align into a single solid line at a second time during the time period; (5) temporal variation of the pattern during the time period may include rotation of the pattern; (6) the mask may comprise a pinhole pair mask; (7) the apparatus may be bi-ocular, and the first set of visual stimuli may be presented to the first eye but not the second eye while the second set of visual stimuli is presented to the second eye but not the first eye; (7) the apparatus may be bi-ocular, and the first set of visual stimuli may be presented to both the first and second eyes while the second set of visual stimuli is presented to the second eye but not the first eye; and (8) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; and (c) a plurality of optical elements, including a first set of optical fibers, a second set of optical fibers and other sets of optical fibers; wherein (i) the first set of optical fibers terminates at a first optical distance from the first eye, and the second set of optical fibers terminates at a second optical distance from the first eye, and (ii) the plurality of optical elements are configured to, during a time period, modify light from the first light source to display a first set of visual stimuli to the first eye to change accommodation of the first eye, while modifying light from the second light source to display a second set of visual stimuli to the first or second eye to measure refractive aberration of the first or second eye, such that (A) at a first time during the time period, the first set of stimuli includes light that passes through the first set of optical fibers but does not include light that passes through the second set of optical fibers, (B) at a second time during the time period, the first set of stimuli includes light that passes through the second set of optical fibers but does not include light that passes through the first set of optical fibers, and (C) the first and second times do not overlap each other. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements (which plurality of optical elements includes a first set of optical fibers, a second set of optical fibers and other sets of optical fiber, the first set of optical fibers terminating at a first optical distance from a first eye of a human, and the second set of optical fibers terminating at a second optical distance from the first eye) such that: (a) during a time period, the plurality of optical elements display a first set of visual stimuli to the first eye to change accommodation of the first eye, while displaying a second set of visual stimuli to the first eye or a second eye of the human to measure refractive aberration of the first or second eye; (b) at a first time during the time period, the first set of stimuli includes light that passes through the first set of optical fibers but does not include light that passes through the second set of optical fibers; (c) at a second time during the time period, the first set of stimuli includes light that passes through the second set of optical fibers but does not include light that passes through the first set of optical fibers; and (d) the first and second times do not overlap each other.

This invention may be implemented as a method of presenting stimuli during a time period to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein: (a) the first set of stimuli includes light that passes through a film and a lens; and (b) the method further comprises changing the distance between the film and the lens at least once during the time period. Furthermore: (1) light in the second set of visual stimuli may pass through a mask before reaching the human; (2) the mask may comprise a light attenuation pattern that varies both spatially and temporally during the time period; (3) the mask may comprise a dash mask; (4) the second set of visual stimuli may apparently comprise two dashed two lines that are apparently separate at a first time during the time period and that apparently align into a single solid line at a second time during the time period; (5) temporal variation of the pattern during the time period may include rotation of the pattern; (6) the mask may comprise a pinhole pair mask; (7) the apparatus may be bi-ocular, and the first set of visual stimuli may be presented to the first eye but not the second eye while the second set of visual stimuli is presented to the second eye but not the first eye; (7) the apparatus may be bi-ocular, and the first set of visual stimuli may be presented to both the first and second eyes while the second set of visual stimuli is presented to the second eye but not the first eye; and (8) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; (c) a plurality of optical elements, including a lens and a film; (d) an actuator; wherein (i) the plurality of optical elements are configured to, during a time period, modify light from the first light source to display a first set of visual stimuli to the first eye to change accommodation of the first eye, while modifying light from the second light source to display a second set of visual stimuli to the first or second eye to measure refractive aberration of the first or second eye, and (ii) the actuator is configured to actuate linear motion of the lens or film to change the distance between the lens and the film at least once during the time period. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements, such that: (a) during a time period, the plurality of optical elements display a first set of visual stimuli to the first eye of a human to change accommodation of the first eye, while displaying a second set of visual stimuli to the first eye or a second eye of the human to measure refractive aberration of the first or second eye; (b) the first set of stimuli includes light that passes through a film and a lens; and (c) the distance between the film and the lens changes at least once during the time period, wherein the plurality of optical elements includes the film and the lens.

This invention may be implemented as a method of presenting stimuli during a time period to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein: (a) the first set of stimuli includes light that passes through a film and an adjustable lens; and (b) the method further comprises changing optical power of the adjustable lens at least once during the time period. Furthermore: (1) light in the second set of visual stimuli may pass through a mask before reaching the human; (2) the mask may comprise a light attenuation pattern that varies both spatially and temporally during the time period; (3) the mask may comprise a dash mask; (4) the second set of visual stimuli may apparently comprise two dashed two lines that are apparently separate at a first time during the time period and that apparently align into a single solid line at a second time during the time period; (5) temporal variation of the pattern during the time period may include rotation of the pattern; (6) the mask may comprise a pinhole pair mask; (7) the apparatus may be bi-ocular, and the first set of visual stimuli may be presented to the first eye but not the second eye while the second set of visual stimuli is presented to the second eye but not the first eye; (7) the apparatus may be bi-ocular, and the first set of visual stimuli may be presented to both the first and second eyes while the second set of visual stimuli is presented to the second eye but not the first eye; and (8) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; and (c) a plurality of optical elements, including a film and an adjustable lens; wherein (i) the plurality of optical elements are configured to, during a time period, modify light from the first light source to display a first set of visual stimuli to the first eye to change accommodation of the first eye, while modifying light from the second light source to display a second set of visual stimuli to the first or second eye to measure refractive aberration of the first or second eye, and (ii) the adjustable lens is configured to change optical power of the adjustable lens at least once during the time period. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements, such that: (a) during a time period, the plurality of optical elements display a first set of visual stimuli to the first eye of a human to change accommodation of the first eye, while displaying a second set of visual stimuli to the first eye or a second eye of the human to measure refractive aberration of the first or second eye; (b) the first set of stimuli includes light that passes through a film and an adjustable lens; and (c) optical power of the adjustable lens changes at least once during the time period, wherein the plurality of optical elements includes the adjustable lens.

This invention may be implemented as a method of presenting stimuli during a time period to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein: (a) a first lens has a first optical power and a second lens has a second optical power and the first and second optical powers are different; (b) the method further comprises using a lens holder to releasably support the first lens during a first portion of the time period, and using the lens holder to releasably support the second lens during a second portion of the time period; such that (i) during the first portion of the time period, the first set of stimuli includes light that has passed through the film and the first lens, but not through the second lens, and (ii) during the second portion of the time period, the first set of stimuli includes light that has passed through the film and the second lens, but not through the first lens. Furthermore: (1) light in the second set of visual stimuli may pass through a mask before reaching the human; (2) the mask may comprise a light attenuation pattern that varies both spatially and temporally during the time period; (3) the mask may comprise a dash mask; (4) the second set of visual stimuli may apparently comprise two dashed two lines that are apparently separate at a first time during the time period and that apparently align into a single solid line at a second time during the time period; (5) temporal variation of the pattern during the time period may include rotation of the pattern; (6) the mask may comprise a pinhole pair mask; (7) the apparatus may be bi-ocular, and the first set of visual stimuli may be presented to the first eye but not the second eye while the second set of visual stimuli is presented to the second eye but not the first eye; (7) the apparatus may be bi-ocular, and the first set of visual stimuli may be presented to both the first and second eyes while the second set of visual stimuli is presented to the second eye but not the first eye; and (8) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; (c) a plurality of optical elements, including a first lens and a second lens; and (d) a lens holder; wherein (i) the plurality of optical elements are configured to, during a time period, modify light from the first light source to display a first set of visual stimuli to the first eye to change accommodation of the first eye, while modifying light from the second light source to display a second set of visual stimuli to the first or second eye to measure refractive aberration of the first or second eye, and (ii) the lens holder is configured for releasably holding the first lens during a first portion of the time period and releasably holding the second lens during a second portion of the time period, such that (A) during the first portion of the time period, the first set of stimuli includes light that has passed through the film and the first lens, but not through the second lens, and (B) during the second portion of the time period, the first set of stimuli includes light that has passed through the film and the second lens, but not through the first lens. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as a method of presenting stimuli during a time period to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein: (a) the first set of stimuli or the second set of stimuli includes light that passes through both a first mask and a second mask; (b) the light that passes through both the first and second masks is used to form a DAF image; and (c) apparent depth of the DAF image changes at least once during the time period. Furthermore: (1) the first mask and second mask may each comprise a pinhole mask; (2) the first mask and second mask may each comprise a light attenuation pattern that varies both spatially and temporally during the time period; (3) the first mask may comprise a first light attenuation pattern and the second mask may comprise a second light attenuation pattern; and the first and second patterns may be identical, except that during at least a portion of the time period (i) scale of the first mask is different than scale of the second mask, and (ii) the first pattern comprises only part of the second pattern or the second pattern comprises only part of the first pattern; (4) the first mask and second mask may each comprise a pinhole mask; (5) the apparatus may be bi-ocular, and the first set of visual stimuli may be presented to the first eye but not the second eye while the second set of visual stimuli is presented to the second eye but not the first eye; (6) the apparatus may be bi-ocular, and the first set of visual stimuli may be presented to both the first and second eyes while the second set of visual stimuli is presented to the second eye but not the first eye; and (7) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; and (c) a plurality of optical elements, including a first mask and a second mask; wherein the plurality of optical elements are configured to, during a time period, modify light from the first light source to display a first set of visual stimuli to the first eye to change accommodation of the first eye, while modifying light from the second light source to display a second set of visual stimuli to the first or second eye to measure refractive aberration of the first or second eye, such that (i) the first set of stimuli or the second set of stimuli includes light that passes through both the first mask and the second mask; (ii) the light that passes through both the first and second masks is used to form a DAF image, and (iii) apparent depth of the DAF image changes at least once during the time period. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements, such that: (a) during a time period, the plurality of optical elements display a first set of visual stimuli to the first eye of a human to change accommodation of the first eye, while displaying a second set of visual stimuli to the first eye or a second eye of the human to measure refractive aberration of the first or second eye; (b) the first set of stimuli or the second set of stimuli includes light that passes through both a first mask and a second mask; (c) the light that passes through both the first and second masks is used to form a DAF image, and (d) apparent depth of DAF image changes at least once during the time period.

This invention may be implemented as a method of presenting stimuli during a time period to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein: (a) the first set of stimuli or the second set of stimuli includes light that passes through both a mask and a lenslet array; (b) the light that passes through both the mask and the lenslet array is used to form an image of a virtual object; and (c) apparent depth of the virtual object changes at least once during the time period. Furthermore: (1) the mask may comprise a light attenuation pattern that varies both spatially and temporally during the time period; (2) the apparatus may be bi-ocular, and the first set of visual stimuli may be presented to the first eye but not the second eye while the second set of visual stimuli is presented to the second eye but not the first eye; (3) the apparatus may be bi-ocular, and the first set of visual stimuli may be presented to both the first and second eyes while the second set of visual stimuli is presented to the second eye but not the first eye; and (4) the apparatus may be monocular, and both the first and second sets of visual stimuli may be presented to the first eye at the same time.

This invention may be implemented as apparatus for presenting stimuli to a human who has a first eye and a second eye, the apparatus comprising in combination: (a) a first light source; (b) a second light source; and (c) a plurality of optical elements, including a first mask and a second mask; wherein the plurality of optical elements are configured to, during a time period, modify light from the first light source to display a first set of visual stimuli to the first eye to change accommodation of the first eye, while modifying light from the second light source to display a second set of visual stimuli to the first or second eye to measure refractive aberration of the first or second eye, such that (i) the first set of stimuli or the second set of stimuli includes light that passes through both a mask and a lenslet array, (ii) the light that passes through both the mask and the lenslet array is used to form an image of a virtual object, and (iii) apparent depth of the virtual object changes at least once during the time period. Furthermore: (1) the apparatus may be bi-ocular, and may be configured to present the first set of visual stimuli to the first eye but not the second eye while presenting the second set of visual stimuli to the second eye but not the first eye; (2) the apparatus may be bi-ocular, and may be configured to present the first set of visual stimuli to both the first and second eyes while presenting the second set of visual stimuli to the second eye but not the first eye; (3) the apparatus may be monocular, and may be configured to present both the first and second sets of visual stimuli to the first eye at the same time; (4) the apparatus may include a first optical channel for presenting stimuli to the first eye and a second optical channel for presenting stimuli to the second eye, and may include an actuator for changing distance between the first and second optical channels.

This invention may be implemented as tangible machine-readable media with instructions encoded thereon for one or more processors to control one or more optical elements out of a plurality of optical elements, such that: (a) during a time period, the plurality of optical elements display a first set of visual stimuli to the first eye of a human to change accommodation of the first eye, while displaying a second set of visual stimuli to the first eye or a second eye of the human to measure refractive aberration of the first or second eye; (b) the first set of stimuli or the second set of stimuli includes light that passes through both a mask and a lenslet array; (c) the light that passes through both the mask and the lenslet array is used to form an image of a virtual object; and (d) apparent depth of the virtual object changes at least once during the time period.

CONCLUSION

While exemplary implementations are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention. Numerous modifications may be made by one of ordinary skill in the art without departing from the scope of the invention.

What is claimed is:

1. A method of presenting stimuli to a human who has a first eye and a second eye, which method comprises using optical apparatus to display a first set of visual stimuli to the first eye to change accommodation of the first eye, while using the apparatus to display a second set of visual stimuli to the first or second eye to measure refractive aberration of the first or second eye, wherein:
   (a) the second set of visual stimuli (i) includes light that passes through a first region of a mask and (ii) includes light that passes through a second region of the mask, which first and second regions of the mask do not overlap each other; and
   (b) the method further comprises using one or more color filters to cause the light that passes through the first region of the mask to be only light of a first set of colors and the light that passes through the second region of the mask to be only light of a second set of colors, wherein the first and second set of colors do not fully overlap.

2. The method of claim 1, wherein:
   (a) light passes through a first tube, but not a second tube, before reaching the first eye; and
   (b) light passes through the second tube, but not the first tube, before reaching the second eye.

3. The method of claim 1, wherein the mask comprises a light attenuation pattern that varies both spatially and temporally during a time period.

4. The method of claim 3, wherein:
   (a) the mask includes pinholes;
   (b) the pinholes consist of a first sequence of pinholes and a second sequence of pinholes;
   (c) the first sequence of pinholes comprises a first dashed line that is straight, and the second sequence of pinholes comprises a second dashed line that is straight; and
   (d) the first and second lines are offset from each other.

5. The method of claim 3, wherein the second set of visual stimuli apparently comprises two dashed two lines that are apparently separate at a first time during the time period and that apparently align into a single solid line at a second time during the time period.

6. The method of claim 3, wherein temporal variation of the pattern during the time period includes rotation of the pattern.

7. The method of claim 6, wherein the mask comprises a pinhole pair mask.

8. The method of claim 1, wherein:
(a) the apparatus is bi-ocular; and
(b) the first set of visual stimuli is presented to the first eye but not the second eye while the second set of visual stimuli is presented to the second eye but not the first eye.

9. The method of claim 1, wherein:
(a) the apparatus is bi-ocular; and
(b) the first set of visual stimuli is presented to both the first and second eyes while the second set of visual stimuli is presented to the second eye but not the first eye.

10. The method of claim 1, wherein:
(a) the apparatus is monocular; and
(b) both the first and second sets of visual stimuli are presented to the first eye at the same time.

11. Apparatus for presenting stimuli to a human who has a first eye and a second eye, the apparatus comprising in combination:
(a) a first light source;
(b) a second light source; and
(c) a plurality of optical elements, including (i) a mask, and (ii) one or more color filters;
wherein
(i) the plurality of optical elements are configured to modify light from the first light source to display a first set of visual stimuli to the first eye to change accommodation of the first eye, while modifying light from the second light source to display a second set of visual stimuli to the first or second eye to measure refractive aberration of the first or second eye,
(ii) the mask is positioned such that the second set of visual stimuli (A) includes light that passes through a first region of the mask and (B) includes light that passes through a second region of the mask, which first and second regions of the mask do not overlap each other, and
(iii) the one or more color filters are configured to cause the light that passes through the first region of the mask to be only light of a first set of colors and the light that passes through the second region of the mask to be only light of a second set of colors, wherein the first and second set of colors do not fully overlap.

12. The apparatus of claim 11, wherein the apparatus:
(a) is bi-ocular; and
(b) is configured to present the first set of visual stimuli to the first eye but not the second eye while presenting the second set of visual stimuli to the second eye but not the first eye.

13. The apparatus of claim 11, wherein the apparatus:
(a) is bi-ocular; and
(b) is configured to present the first set of visual stimuli to both the first and second eyes while presenting the second set of visual stimuli to the second eye but not the first eye.

14. The apparatus of claim 11, wherein the apparatus:
(a) is monocular; and
(b) is configured to present both the first and second sets of visual stimuli to the first eye at the same time.

15. The apparatus of claim 11, wherein the apparatus:
(a) includes a first optical channel for presenting stimuli to the first eye and a second optical channel for presenting stimuli to the second eye; and
(b) includes an actuator for changing distance between the first and second optical channels.

\* \* \* \* \*

UNITED STATES PATENT AND TRADEMARK OFFICE
CERTIFICATE OF CORRECTION

PATENT NO.         : 9,844,323 B2
APPLICATION NO.    : 14/906272
DATED              : December 19, 2017
INVENTOR(S)        : Vitor Pamplona et al.

It is certified that error appears in the above-identified patent and that said Letters Patent is hereby corrected as shown below:

The Assignee was erroneously listed as: Massachusetts Institute of Technology, Cambridge, MA (US)
    The correct Assignee is: EyeNetra, Inc., Cambridge, MA (US)

Signed and Sealed this
Twenty-second Day of May, 2018

Andrei Iancu
*Director of the United States Patent and Trademark Office*